United States Patent [19]

Hasty et al.

[11] Patent Number: 5,955,644
[45] Date of Patent: *Sep. 21, 1999

[54] KU DEFICIENT CELLS AND NON-HUMAN TRANSGENIC ANIMALS

[75] Inventors: Paul Hasty, Magnolia; Dae-sik Lim, Houston, both of Tex.

[73] Assignee: M.D. Anderson Cancer Center, Houston, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/695,866

[22] Filed: Aug. 8, 1996

[51] Int. Cl.$^6$ .............................. C12N 5/00; C12N 15/00
[52] U.S. Cl. ......................... 800/18; 435/325; 435/354; 435/440; 435/455
[58] Field of Search .............................. 800/2, DIG. 1–5, 800/18; 435/172.3, 325, 440, 455, 354; 536/23.1

[56] References Cited

U.S. PATENT DOCUMENTS

| | | | |
|---|---|---|---|
| 4,873,191 | 10/1989 | Wagner et al. | 435/172.3 |
| 5,162,215 | 11/1992 | Bosselman et al. | 435/172.3 |
| 5,464,764 | 11/1995 | Capecchi et al. | 435/172.3 |
| 5,545,808 | 8/1996 | Hew et al. | 800/2 |

FOREIGN PATENT DOCUMENTS

| | | |
|---|---|---|
| 0 386 563 A1 | 2/1990 | European Pat. Off. . |
| WO 90/13641 | 11/1990 | WIPO . |
| WO 91/04753 | 4/1991 | WIPO . |
| WO 91/09865 | 7/1991 | WIPO . |
| WO 91/11535 | 8/1991 | WIPO . |

OTHER PUBLICATIONS

Pursel et al. Genetic Engineering of Livestock. Science, vol. 244, pp. 1281–1288, Jun. 16, 1989.

Nussenzweig et al. Requirement for Ku80 in growth and immunoglobulin V(D)J recombination. Nature, vol. 382, pp. 551–555, Aug. 8, 1996.

Houdebine, Louis–Marie. Production of pharmaceutical proteins from transgenic animals. J. of Biotech. vol. 34, pp. 269–287, 1994.

Wilmut et al., 1988, "A Revolution in Animal Breeding", *New Scientist,* pp. 56–59.

Fassler et al. Knockout Mice: How to make them and why. Int. Arch. Allergy Immunol., vol. 106, pp. 323–334, 1995.

Bradley et al. Modifying the mouse: Design and Desire. Bio/Technology, vol. 10, pp. 534–538, May 1992.

Jeggo et al., 1995, "Manage a trois: Double strand break repair, V(D)J recombination and DNA–PK," *Bioessays* 17:949–957.

Zhu et al., 1996, "Ku86 deficient mice exhibit severe combined immunodeficiency and defective processing of V(D)J recombination intermediates," *Cell* 86:379–389.

Adra et al., 1987, "Cloning and expression of the mouse pgk–1 gene and the nucleotide sequence of its promoter", *Gene* 60:65–74.

Baker et al., 1995, "Male Mice Defective in the DNA Mismatch Repair Gene PMS2 Exhibit Abnormal Chromosome Synapsis in Meiosis", *Cell* 82:309–319.

Bayreuther et al., 1988, "Human skin fibroblasts in vitro differentiate along a terminal cell lineage", Proc. Natl. Acad. Sci. USA 85:5112–5116.

Biedermann et al., 1991, "scid mutation in mice confers hypersensitivity to ionizing radiation and a deficiency in DNA double–strand break repair", Proc. Natl. Acad. Sci. USA 88:1394–1397.

Blunt et al., 1995, "Defective DNA–Dependent Protein Kinase Activity Is Linked to V(D)J Recombination and DNA Repair Defects Associated with the Murine scid Mutation", *Cell* 80:813–823.

Bogue et al., 1996, "p53 is required for both radiation–induced differentiation and rescue of V(D)J rearrangement in said mouse thymocytes" Genes Dev. 10:553–565.

Bolivar et al., 1977, "Construction and Characterization of New Cloning Vehicles: II. A Multipurpose Cloning System" *Gene* 2:95–113.

Bosma et al., 1983, "A severe combined immunodeficiency mutation in the mouse", Nature 301:527–530.

Boubnov et al., 1995, "Complementation of the ionizing radiation sensitivity, DNA end binding, and V(D)J recombination defects of double–strand break repair mutants by the p86 Ku autoantigen", Proc. Natl. Acad. Sci. USA 92:890–894.

Bradley, 1987, In "Teratocarcinomas and embryonic stem cells: a practical approach", E. Robertson, ed. (Oxford: IRL Press), pp. 113–151.

Broder et al., "Antiretroviral Therapy in AIDS", Ann. Int. Med. 113:604–618.

Campisi, 1996, "Replicative Senescence: An Old Lives' Tale?", *Cell* 84:497–500.

Carroll and Bosma, 1991, "T–lymphocyte development in scid mice is arrested shortly after the initiation of T–cell receptor δ gene recombination", Genes Dev. 5:1357–1366.

(List continued on next page.)

*Primary Examiner*—Brian R. Stanton
*Assistant Examiner*—Deborah J. R. Clark
*Attorney, Agent, or Firm*—Pennie & Edmonds LLP

[57] ABSTRACT

Ku deficient cells and transgenic animals are described that comprise at least one allele of the XRCC5 gene that has been mutated by targeted disruption. Fibroblasts derived from XRCC5 mutant embryos and mice were found to prematurely age. These cells displayed decreased growth, slow entry into S phase, altered colony size distribution that favored small colonies, short life span and morphology characteristic of terminal differentiation. Mutant cells were also hypersensitive to γ-radiation. The tissue culture data was at least partly reproduced in vivo because mutant mice grew slower than control littermates. The XRCC5 mutation, designated xrcc5$^{M1}$, was a deletion of nucleotides 701–964 that shifted the reading frame. xrcc5$^{M1}$ is expected to be null because the deleted allele produced no detectable transcript and because lymphocyte development and V(D)J recombination was severely disrupted.

15 Claims, 21 Drawing Sheets

OTHER PUBLICATIONS

Ch'ng et al., 1989, "Antisense RNA complementary to 3' coding and noncoding sequences of creatine kinase is a potent inhibitor of translation in vivo", Proc. Natl. Acad. Sci. USA 86:10006–10010.

Cleaver, 1994, "It Was A Very Good Year for DNA Repair", Cell 76:1–4.

de Vries et al., 1995, "Increased susceptibility to ultraviolet–B and carcinogens of mice lacking the DNA excision repair gene XPA", Nature 377:169–173.

de Wind et al., 1995, "Inactivation of the Mouse Msh2 Gene REsults in Mismatch Repair Deficiency, Methylation Tolerance, Hyperrecombination, and Predisposition to Cancer", Cell 82:321–330.

Donehower et al., 1992, "Mice deficient for p53 are developmentally normal but susceptible to spontaneous tumours", Nature 356:215–221.

Drapkin et al., 1994, "Where Transcription Meets Repair", Cell 77:9–12.

Errami et al., 1996, "Ku86 Defines the Genetic Defect and Restores X–Ray Resistance and V(D)J Recombination to Complementation Group 5 Hamster Cell Mutants", Mol. Cell. Biol. 16: 1519–1526.

Evans et al., 1981, "Establishment in culture of pluripotential cells from mouse embryos", Nature 292:154–156.

Finnie et al., 1995, "DNA–dependent protein kinase activity is absent in xrs–6 cells: Implications for site–specific recombination and DNA double–strand break repair", Proc. Natl. Acad. Sci. USA 92:320–324.

Friedberg, et al. 1995, DNA repair and mutagenesis, pp. 147–192, ASM Press Washington, D. C.

Friedberg, 1992, "Xeroderma Pigmentosum, Cockayne's Syndrome, Helicases, and DNA Repair: What's the Relationship?", Cell 71:887–889.

Fulop and Phillips, 1990, "The scid mutation in mice causes a general defect in DNA repair", Nature 347:479–482.

Gottlieb and Jackson, 1994, "Protein kinases and DNA damage", Trends Biochem. Sci. 19:500–503.

Hartley et al., 1995, "DNA–Dependent Protein Kinase Catalytic Subunit: A Relative of Phosphatidylinositol 3–Kinase and the Ataxia Telangiectasia Gene Product", Cell 82:849–856.

Hasty et al., 1991, "Target Frequency and Integration Pattern for Insertion and Replacement Vectors in Embryonic Stem Cells", Molecular and Cellular Biology 11:4509–4517.

Hasty et al., 1991, "Introduction of a subtle mutation into the Hox–2.6 locus in embryonic stem cells", Nature 350:243–246.

Helene., C. and Toulme, J., 1990, "Specific regulation of gene expression by antisense, sense and antigene nucleic acids", Biochimica Bioshys. Acta 1049:99–125.

Hunter, 1995, "When Is a Lipid Kinase Not a Lipid Kinase? When It Is a Protein Kinase", Cell 83:1–4.

Jeggo, 1990, "Studies on mammalian mutants defective in rejoining double–strand breaks in DNA", Mutation Research 239:1–16.

Jeggo, 1985, "X–Ray sensitive mutants of Chinese hamster ovary cell line: radio–sensitivity of DNA synthesis", Mutation Research 145:171–176.

Joyner et al., 1989, "Production of a mutation in mouse En–2 gene by homologous recombination in embryonic stem cells", Nature 338:153–156.

Kastan et al., 1992, "Participation of p53 Protein in the Cellular Response to DNA Damage", Cancer Res. 51:6304–6311.

Kirchgessner et al., 1995, "DNA–Dependent Kinase (p350) as a Candidate Gene for the Murine SCID Defect", Science 267:1178–1182.

Krogstad and Champoux, 1990, "Sequence–Specific Binding of DNA by the Moloney Murine Leukemia Virus Integrase Protein", J. Virol. 64:2796–2801.

Kuhn et al., 1995, "DNA–dependent protein kinase: a potent inhibitor of transcription by RNA polymerase I", Genes Dev. 9:193–203.

Lee et al., 1995, "Isolation of mammalian cell mutants that are X–ray sensitive, impaired in DNA double–strand break repair and defective V(D)J recombination", Mutation Research 336:279–291.

Lees–Miller et al., 1995, "Absence of p350 Subunit of DNA–Activated Protein Kinase from a Radiosensitive Human Cell Line", Science 267:1183–1185.

Lehmann and Carr, 1995, "The ataxia–talangiectasia gene: a link between checkpoint controls, neurodegeneration and cancer", Trends in Genet. 11:375–377.

Li et al., 1995, The XRCC4 Gene Encodes a Novel Protein Involved in DNA Double–Strand Break Repair and V(D)J Recombination, Cell 83:1079–1089.

Loreau et al., 1990, "Blockage of AMV reverse transcriptase by antisense oligodeoxynucleotides", FEBS Letters 274:53–56.

Mansour et al., 1988, "Disruption of the proto–oncogene int–2 in mouse embryo–derived stem cells: a general strategy for targeting mutations to non–selectable genes", Nature 336:348–352.

McBlane et al., 1995, "Cleavage at a V(D)J Recombination Signal Requires Only RAG1 and RAG2 Proteins and Occurs in Two Steps", Cell 83:387–395.

Meyn, 1993, "High Spontaneous Intrachromosomal Recombination Rates in Ataxia–Telangiectasia", Science 260:1327–1330.

Mielke et al., 1995, "A simple assay for puromycin N–acetyltransferase: selectable marker and reporter", Trend. Genet. 11:258–259.

Munir et al., 1990, "Antisense RNA Production in Transgenic Mice", Somat. Cell Mol. Genet. 16:383–394.

Nakane et al., 1995, High incidence of ultraviolet–B–or chemical–carcinogen–induced skin tumours in mice lacking Nature 377:165–168.

Pennycook et al., 1993, "High Frequency of Normal $DJ_H$ Joints in B Cell Progenitors in Severe Combined Immunodeficiency Mice", J. Exp. Med. 178:1007–1016.

Pepin et al., 1991, "Impaired type II glucocorticoid–receptor function in mice bearing antisense RNA transgene", Nature 355:725–728.

Pergola et al., 1993, "V(D)J Recombination in Mammalian Cell Mutants Defective in DNA Double–Strand Break Repair", Mol. Cell. Biol. 13:3464–3471.

Petes et al., 1991, Recombination in yeast, In: *The Molecular and Cellular Biology the Yeast Saccharomyces* (eds. J. R. Broach, J. R. Pringle, and E. W. Jones), pp. 407–521, Cold Spring Harbor Laboratory Press, Cold Spring Harbor, New York.

Pfarr et al., 1986, "Differential Effects of Polyadenylation Regions on Gene Expression in Mammalian Cells", DNA 5:115–122.

Ramirez–Solis et al, 1992, "Genomic DNA Microextraction: A Method to Screen Numerous Samples", Anal. Biochem. 201:331–335.

Ramsden and Gellert, 1995, "Formation and resolution double–strand break intermediates in V(D)J rearrangement", Genes Dev. 9:2409–2420.

Robertson, 1987, In "Teratocarcinomas and embryonic stem cells: a practical approach", E. J. Robertson, ed. (Oxford: IRL Press), pp. 71–112.

Roth et al., 1995, "How to make ends meet", Current Biology 5:496–499.

Roth et al., 1993, "Characterization of broken DNA molecules associated with V(D)J recombination", Proc. Natl. Acad. Sci. USA 90:10788–10792.

Roth et al., 1992, "V(D)J Recombination: Broken DNA Molecules with Covalently Sealed (Hairpin) Coding Ends in scid Mouse Thymocytes", Cell 70:983–991.

Sands et al., 1995, "High susceptibility to ultraviolet–induced carcinogenesis in mice lacking XPC", Nature 377:162–165.

Savitsky et al., 1995, "A Single Ataxia Telangiectasia Gene with Product Similar to PI–3 Kinase", Science 268:1749–1753.

Schlissel et al., 1993, "Double–strand signal sequence breaks in V(D)J recombination are blunt, 5'–phosphorylated, RAG–dependent, and cell cycle regulated", Genes Dev. 7:2520–2532.

Schuler et al., 1986, "Rearrangement of Antigen Receptor Genes Is Defective in Mice with Severe Combined Immune Deficiency", Cell 46:963–972.

Schwartzberg et al., 1989, "Germ–Line Transmission of a c–abl Mutation Produced by Targeted Gene Disruption in ES Cells", Science 246:799–803.

Sekiguchi et al., 1983, "Recovery of a hybrid vector, derived from bovine papilloma virus DNA, pBR322 and the HSV tk gene, by bacterial transformation with extrachromosomal DNA from transfected rodent cells", Gene 21:267–272.

Smider et al., 1994, "Restoration of X–ray Resistance and V(D)J Recombination in Mutant Cells by Ku cDNA", Science 266:288–291.

Smith et al., 1980, "Colony Size Distribution As A Measure Of Age In Cultured Human Cells. A Brief Note." Mech. Age Dev. 6:282–286.

Smith et al., 1978, "Colony size distributions as a measure of in vivo and in vitro aging", Proc. Natl. Acad. Sci., USA 75:1353–1356.

Stout et al., 1990, "Antisense RNA Inhibition of HPRT Synthesis", Somat. Cell Mol. Genet. 16:369–382.

Taccioli et al., 1993, "Impairment of V(D)J Recombination in Double–Strand Break Repair Mutants", Science 260:207–210.

Taylor et al., 1975, "Ataxia telangiectasia: a human mutation with abnormal radiation sensitivity", Nature 258:427–429.

van Gent et al., 1995, "Initiation of V(D)J Recombination in a Cell–Free System", Cell 81:925–934.

von Melchner et al., "Selective disruption of genes expressed in totipotent embryonal stem cells", Genes and Development 6:919–927.

Weaver, 1995, "What to do at an end: DNA double–strand–break repair", Trends in Genet. 11:388–392.

Wiler et al., 1995, "Equine severe combined immunodeficiency: A defect in V(D)J recombination and DNA–dependent protein kinase activity", Proc. Natl. Acad. Sci. 92:11485–11489.

Zakian, 1995, "ATM–Related Genes: What Do They Tell Us about Functions of the Human Gene?", Cell 82:685–687.

Zhu and Roth, 1995, "Characterization of Coding Ends in Thymocytes of scid Mice: Implications for the Mechanism of V(D)J Recombination", Immunity 2:101–112.

Zjilstra et al., 1989, "Germ–line transmission of a disrupted $\beta_2$–microglobulin gene produced by homologous recombination in embryonic stem cells", Nature 342:435–438.

E17.5

Control    xrcc5$^{M1-/-}$

3 Weeks

Control xrcc5$^{M1-/-}$

Control xrcc5$^{M1}$

Control xrcc5$^{M1}$

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 2515 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
AAGTAATCAA ATCACCTGAG GACCAGCATG GCGTGGTCGG TAAATAAGGC AGCTGTTGTG    60
CTGTGTGTGG ATGTGGGGGT TGCCATGGGT AACTCCATTC CTGGTGAAGA ATCTCCAATT   120
GAACAAGCAA AGAAAGTGAT GACTATGTTT GTCCAACGAC AGGTATTTTC GGAGAGCAAA   180
GATGAGATTG CGTTAGCTCT CTATGGCACA GATGGCACTG ATATGCCCCT TTCTGGCAAG   240
GACCAGTATC AGAACATCAC AGTGTGCAGA CACCTGATGC TACCAGATTT TGATTTGCTG   300
GAAGACATCG GAAACAAAAT CCAGCCAAGT TCCCAGCAAG CCGACTTCCT GGACGCCCTG   360
ATTGTGTGCA TGGATTTGAT TCAGCGTGAA ACCATAGGGA AGAAGTTTGG GAAGAAGCAT   420
ATTGAAGTGT TCACTGACCT CCGCAGCCCG TTCAGCAAGG ACCAACTGGA CGTTATAATT   480
TGTAACTTGA AGAAGTGTGG CATCTCTCTG CAGTTCTTTT TGCCTTTTCC AATCGACAAG   540
AATGGCGAGC CTGGCGAGAG AGGGGACCTG GACTCTGGCT TGGACCACCT CAAACCCTCC   600
TTTCCTCAAA AAGGACTTAC TGAGCAGCAA AAGGAAGGCA TCCGCATGGT GACAAGGGTG   660
ATGCTGTCCT TAGAAGGCGA AGACGGGCTG GATGAAATTT ATTCCTTTAG TGAGAGTCTA   720
CGACAACTGT GCGTCTTTAA GAAGATTGAG AGGCGTTCCA TGCCCTGGCC CTGCCAACTG   780
ACCATTGGCC CCAACTTGTC TATAAAGATT GTAGCCTATA ATCGATTGT ACAGGAGAAA   840
TTTAAGAAGA GTTGGGTAGT TGTGGACGCA AGAACGCTAA AGAAGGAAGA TATACAAAAA   900
GAGACTGTTT ATTGCCTAAA TGACGATGAT GAAACTGAAG TTTCCAAAGA GGACACTATT   960
CAAGGGTACC GCTACGGAAG TGATATCATT CCTTTTTCTA AAGTGGATGA GGAACAAATG  1020
AAATATAAAT CTGAGGGGAA GTGCTTCTCT GTTTTGGGAT TTTGTAAATC TTCTCAGGTT  1080
CATAGAAGAT TCTTCATGGG ACATCAAGTT CTAAAGGTCT TTGCAGCAAA GGATGATGAG  1140
GCGGCAGCTG TTGCCCTTTC CTCCCTCGTT CATGCTTTGG ATGAGTTAAA CATGGTCGCC  1200
ATCGTCCGAT ATGCTTATGA CAAAAGATCT AATCCTCAAG TTGGTGTAGC TTCCCTTTAC  1260
ATTAAGGACG CCTATGAGCG TTTAGTTTAT GTGCAGCTGC CTTTCATGGA AGACTTGCGG  1320
CAATACATGT TTTCCTCGCT GAAAAACAAT AAGAAGTGCA CTCCCACAGA GGCCCAGCTG  1380
AGCGCTATTG ATGATCTGAT TGATTCCATG AGCTTGGTAA AGAAAAACGG GGAAGAAGAC  1440
ATTGTTGAAG ATTTGTTTCC GGCCTCCAAA ATTCCAAATC CTGAATTTCA GCGATTGTAC  1500
CAGTGTCTGC TGCATAGAGC CTTACATCTC CAGGAGCGGC TGCCCCCGAT TCAGCAGCAC  1560
ATTTTGAATA TCTGGGATCC CCCCACTGAG ATGAAGCAAA AATGTGAGAG TCCACCCCTT  1620
AAAGTAAAGA CCCTTTTCCC TCTCACAGAA GTCATCAAGA AAAAGAACCA AGTGACTGCT  1680
CAGGACGTTT TCCAAGACAA TCATGAAGAG GGGCCCGCTG CTAAAAAATA TAAAACTGAG  1740
AAAGAAGAAG ATCACATCAG CATCTCCAGC CTGGCAGAAG GGAACATCAC CAAGGTTGGA  1800
```

```
AGTGTGAATC CTGTTGAAAA CTTCCGTTTC CTAGTAAGAC AGAAGATTGC CAGCTTTGAG  1860

GAAGCGAGTC TCCAGTTAAT AAGTCACATC GAACAATTTT TGGATACCAA TGAAACACTG  1920

TATTTTATGA AAAGTATGGA CTGCATCAAA GCTTTCCGGG AGGAGGCCAT TCAGTTTTCA  1980

GAAGAACAGC GCTTCAACAG CTTCCTGGAA GCCCTTCGAG AGAAAGTGGA AATTAAGCAA  2040

TTAAATCATT TCTGGGAAAT TGTTGTTCAG GATGGAGTTA CTCTGATCAC CAAAGACGAA  2100

GCCCCAGGAA GCTCTATCAC AGCTGAGGAA GCCAAAAAGT TTCTGGCCCC CAAAGACAAA  2160

GCAAAAGAAG ATACAACGGG ACCTGAAGAA GCTGGTGATG TGGATGATTT ACTGGACATG  2220

ATATAGATCA TGGATGTGTG GGGAATCCAA GAGTGCCAGC TCTGTGCTGC TGAGAGCTCT  2280

GGCAGCATCC CTGAGGCCGT GCAGGGGATG TGAAGCTCTG GACGTCATCC TAGCAGACAA  2340

CTTGGGAATG AGTCACTCCA GGTCTCTACA GAGTGACCAT AAGGACATAT ATTACAAGAA  2400

ATAACTTAGA CCCTATTCAA AATTTATAAA AGAGCCATTA TTTTTCTGAT TGGTAAAAAA  2460

AAAAAAAAAC CGAATTCGGC CGATTCAGCT TGGACTTAAC CAGGCTGAAC TTGCT        2515
```

KU DEFICIENT CELLS AND NON-HUMAN TRANSGENIC ANIMALS

FIELD OF THE INVENTION

The present invention relates to cells and non-human transgenic animals that have been engineered to be deficient in the autoantigen called Ku. Ku activity and DNA dependent protein kinase (DNA-PK) activity was reduced in cells by targeted disruption of the XRCC5 gene which encodes Ku86, also called Ku80, which is one of the subunits of Ku and DNA-PK, and the engineered cells were subsequently used to generate Ku deficient transgenic animals.

BACKGROUND OF THE INVENTION

Cellular DNA normally exists in a dynamic environment. Cellular functions of repair, recombination, replication, and cell cycle regulation are intimately interwoven to maintain genomic stability and generate genetic diversity (reviewed by Petes et al., 1991, Recombination in yeast, In: The Molecular and Cellular Biology the Yeast Saccharomyces (eds. J. R. Broach, J. R. Pringle, and E. W. Jones), pp. 407–521, Cold Spring Harbor Laboratory Press, Cold Spring Harbor, N.Y.; Drapkin et al., 1994, Cell 77:9–12; Kuhn et al., 1995, Genes Dev. 9:193–203; Friedberg, et al. 1995, DNA repair and mutagenesis, pp. 147–192, ASM Press Washington, D. C.; Li et al., 1995, Cell 83:1079–1089). A mutation in a gene whose product is critical to any of these processes may result in a variety of clinical signs that include neurological disorders, immunodeficiency, and predisposition to cancer.

Understanding the molecular mechanisms of repair and recombination will be beneficial to understanding the etiology of diseases associated with defects in these processes. Transgenic animals are useful for studying the dynamic nature of DNA in vivo. In particular, transgenic mice are ideal. The similarities between the genetic constitution and organization of humans and mice are remarkable (Lyon and Searle, 1989, Genetic variants and strains of the laboratory mouse, 2nd ed. Oxford University Press, Oxford). In addition, anatomical similarities between mice and humans provide the opportunity for direct physiological comparison. Targeted disruption of genes encoding protein products such as the p53 tumor suppressor (Donehower et al., 1992, Nature 356:215–221), the mismatch repair proteins (Baker et al., 1995, Cell 82:309–319; de Wind et al., 1995, Cell 82:321–330) and the xeroderma pigmentosa complementation groups (Sands et al., 1995, Nature 377:162–165; de Vries et al., 1995, Nature 377:169–173; Nakane et al., 1995, Nature 377:165–168) have revealed striking similarities to inherited disorders in humans.

A number of different DNA repair pathways are responsible for correcting a variety of specific DNA lesions. These pathways include nucleotide excision repair, mismatch repair and double-strand break (DSB) repair. The mechanisms responsible for nucleotide excision repair and mismatch repair are fairly well understood, and mutations affecting these processes have been characterized (reviewed in Friedberg, 1992 Cell 71:887–889; Cleaver, 1994, Cell 76:1–4). The mechanisms responsible for the repair of DSBs remain poorly understood. Several inherited disorders of mammals feature defects in the repair of DSBs that are associated with hypersensitivity to ionizing radiation and immunodeficiency. These include Ataxia-Telangiectasia (AT) in humans, and autosomal recessive scid (severe combined immunodeficiency) in mice and in horses.

AT is an autosomal recessive defect that results in progressive neurodegeneration, immune deficiencies, susceptibility to cancer, premature aging and permanently dilated blood vessels in the eyes, ears, and parts of the face (reviewed by Lehmann and Carr, 1995, Trends in Genet. 11:375–377). Cells from AT patients may often display chromosomal instability and tend to accumulate chromosomal aberrations. Additionally, "normal" cells temporarily suspend DNA replication after sustaining DNA damage whereas AT cells continue to replicate their DNA in the presence of DNA damage. Cells isolated form AT patients also exhibit an increased rate of intrachromosomal recombination (Meyn, 1993, Science 260:1327–1330) and fail to halt the cell cycle in response to ionizing radiation (Kastan et al., 1992, Cancer Res. 51:6304–6311). AT patients are predisposed to cancer and may be hypersensitive to ionizing radiation (Taylor et al., 1975, Nature 258:427–429). The AT gene was recently cloned (Savitsky et al., 1995, Science 268:1749–1753) and has homology to the phosphatidylinositol (PI) 3-kinases including (reviewed by Zakian, 1995, Cell 82:685–687): Saccharomyces cerevisiae TOR1 and TOR2 (G1-S phase transition), mammalian FRAP and rRAFT (G1-S transition), Schizosaccharomyces pombe RAD3 (rad 3 cells are sensitive to X-ray and ultraviolet light and fail to arrest in G2 after DNA damage), S. cerevisiae MEC1 (required for S-M and G2-M checkpoints and meiotic recombination) and mammalian DNA-$PK_{cs}$ (the catalytic subunit of DNA-PK which is involved in repairing DSBs generated during V(D)J recombination and after exposure to ionizing radiation; see below). The observed homology to these proteins indicates that ATM plays an important role in cell growth and cell cycle regulation. Although these proteins have homology to lipid kinases, they may function as protein kinases (reviewed by Hunter, 1995, Cell 83:1–4). For example, DNA-$PK_{cs}$ has protein kinase activity in vitro, but no lipid kinase activity has been detected (Hartley et al., 1995, Cell 82:849–856).

The scid mutation in mice is recessive and results in an immunodeficiency caused by a failure to repair a specific class of broken DNA ends that arise during rearrangement of T cell receptor (TCR) and immunoglobulin (Ig) genes (V(D)J recombination) in developing lymphocytes (see below). A similar defect has recently been described in Arabian foals (Wiler et al., 1995, Proc. Natl. Acad. Sci. 92:11485–11489). The repair of DSBs created during V(D)J recombination is essential for generating TCR chains (in T cells) and Ig proteins (in B cells). Thus, in scid animals both B and T cell development is arrested at an early stage resulting in immunodeficiency.

V(D)J recombination is responsible for forming the exons that encode the variable regions of TCR and immunoglobulin molecules (reviewed by Roth et al., 1995, Current Biology 5:496–499; Weaver, 1995, Trends in Genet. 11:388–392). Recombination is initiated by the introduction of DSBs at recombination signal sequences that are situated adjacent to the V, D, and J coding elements. Cleavage is performed by the RAG-1 and RAG-2 proteins and generates two types of broken ends: coding ends, which are covalently sealed in the form of hairpins (Roth et al., 1992, Cell 70:983–991; Zhu and Roth, 1995, Immunity 2:101–112) and signal ends, which are blunt (Roth et al., 1993, Proc. Natl. Acad. Sci. U.S.A. 90:10788–10792; Schlissel et al., 1993, Genes Dev. 7:2520–2532). Joining of coding ends assembles the V, D, or J gene segments, forming a rearranged variable region exon (the junction is termed a coding joint) and joining of signal ends forms a reciprocal product termed a signal joint. Recent experiments both in cell-free systems (van Gent et al., 1995, Cell 81:925–934; McBlane et al., 1995, Cell 83:387–395) and in vivo (Ramsden and Gellert, 1995, Genes Dev. 9:2409–2420) have strongly suggested that blunt signal ends and hairpin coding ends are in fact normal intermediates in V(D)J recombination.

Although the characterization of DNA intermediates in vivo and the analysis of the cleavage reaction in vitro have provided important information about the roles of RAG-1 and RAG-2 in the cleavage reaction, the mechanisms responsible for joining signal and coding ends remain unknown. The mouse scid mutation blocks formation of coding joints and is characterized by accumulation of hairpin coding ends (Roth et al., 1992; Zhu and Roth, 1995).

The scid animals and cell lines are also hypersensitive to ionizing radiation due to a failure in repairing DSBs (Fulop and Phillips, 1990, Nature 347:479–482; Biedermann et al., 1991, Proc. Natl. Acad. Sci. U.S.A. 88:1394–1397). This observation provided the first indication that there is overlap between general DSB repair pathways and V(D)J recombination, although subsequently several mutations that affect both processes have now been identified (see Roth et al., 1995 for review).

Recent work has shown that a single protein complex, the DNA-dependent protein kinase (DNA-PK) plays a critical role in both V(D)J recombination and DSB repair. The catalytic subunit of DNA-PK, DNA-PK$_{cs}$, (an ATM homologue) was shown to be a strong candidate for the said defect in mice (Blunt et al., 1995, Cell 80:813–823; Kirchgessner et al., 1995, Science 267:1178–1182; Boubnov et al., 1995, Proc. Natl. Acad. Sci. U.S.A. 92:890–894; Lees-Miller et al., 1995, Science 267:1183–1185) and horses (Wiler et al., 1995).

Additional mutations in cell lines that interfere with both V(D)J recombination and DSB repair were subsequently identified (Pergola et al., 1993, Mol. Cell. Biol. 13:3464–3471; Taccioli et al., 1993, Science 260:207–210). These cell lines comprised four complementation groups, termed XRCC4 through XRCC7. Three of these groups (XRCC5–7) were shown to represent each of the three components of DNA-PK. The observation that three of the four identified mutations that affect DSB repair and V(D)J recombination affect components of DNA-PK suggests that DNA-PK plays a critical role in these processes. DNA-PK is a trimeric molecule composed of Ku, a DNA binding heterodimer consisting of Ku70 and Ku86 subunits and DNA-PK$_{cs}$. XRCC7 appears to encode DNA-PK$_{cs}$ (murine and foal scid). The sxi-1 cell line (XRCC6) can be complemented by a Ku70 cDNA (Weaver, 1995; Lee et al., 1995, Mutation Research 336:279–291). XRCC5 was rescued by Ku86 cDNA (Taccioli et al., 1994; Smider et al., 1994, Science 266:288–291; Boubnov et al., 1995) and genomic deletions were observed that removed part of the Ku86 coding sequence in XRCC5 cells (Errami et al., 1996, Mol. Cell. Biol. 16: 1519–1526). A deficiency in Ku86 resulted in unstable Ku70 that was rescued with expression of Ku86 cDNA (Errami et al., 1996). Therefore, a deficiency of Ku86 lead to a deficiency in Ku70 and a mutation in the sequences that code for either protein should effectively ablate the other. In addition, a Ku86 deficiency lead to no DNA-PK activity (Finnie et al., 1995, Proc. Natl. Acad. Sci. U.S.A. 92:320–324). Therefore, a mutation in sequences that code for Ku86 should effectively ablate DNA-PK$_{cs}$ function; however, there may be Ku function that is independent of DNA-PK$_{cs}$. The XRCC4 gene has recently been shown to encode a novel protein (Li et al., 1995, Cell 83:1079–1089), and xrcc4 mutant cell lines exhibit normal DNA-PK activity.

DNA-PK is activated by DNA lesions and is capable of phosphorylating a variety of substrates, including transcription factors and the p53 tumor suppressor protein. Upon Ku binding to DNA ends, the kinase activity becomes activated, leading to phosphorylation of a variety of protein substrates in vitro (Gottlieb and Jackson, 1994, Trends Biochem. Sci. 19:500–503). It has been suggested that DNA-PK may function to sense DNA damage (Roth et al., 1995). The suggestion that DNA-PK may be involved in cell cycle control fits with the recent observation that the catalytic subunit, DNA-PK$_{cs}$, shares homology with PI 3-kinase family members involved in cell cycle control, DNA repair and DNA damage responses (reviewed by Zakian, 1995). This notion is supported by the observation that Ku deficient cells have a slightly longer cell division time, although no clear-cut cell cycle checkpoint deficiencies have been described (Jeggo, 1985, Mutation Research 145:171–176; Jeggo, 1990, Mutation Research 239:1–16; Lee et al., 1995, Mutation Research 336:279–291).

The references discussed herein are provided solely for their disclosure prior to the filing date of the present application. Nothing herein is to be construed as an admission that the inventors are not entitled to antedate such disclosure by virtue of prior invention.

3.0. SUMMARY OF THE INVENTION

An objective of the present invention is to provide animal cells which are Ku deficient due to a disruption in the Ku86 coding sequences (the XRCC5 gene).

An additional objective of the present invention is to provide non-human transgenic embryos, animals, and offspring which are Ku deficient due to the targeted disruption of the Ku86 coding sequences (the XRCC5 gene).

One specifically exemplified embodiment of the present invention is a diploid animal (mouse) cell containing two chromosomal alleles of the XRCC5 gene, wherein at least one of the alleles has an engineered mutation (i.e., targeted disruption) in the XRCC5 gene that results in the cell producing less than wild-type levels of Ku activity.

An additional embodiment of the present invention is the use of the novel genetically modified Ku deficient cell to generate Ku deficient non-human transgenic embryos and animals.

Another embodiment of the present invention are the Ku deficient non-human, preferably mouse, transgenic embryos and animals that comprise a targeted disruption in the XRCC5 gene, and hence produce less than wild-type levels of Ku activity. The Ku deficient non-human transgenic animals of the present invention may be heterozygous or homozygous for the mutated XRCC5 allele.

4.0. BRIEF DESCRIPTION OF THE DRAWINGS

FIGS. 1(A–D). Targeting strategy for XRCC5. a. The targeting vector was designed to delete XRCC5 genomic sequences including two exons (containing,nucleotides 701–964, Gene Bank accession #X66323, see SEQ ID NO:1) that encode amino acids 229–313. This deletion generates a frameshift mutation after amino acid 313. Boxes represent exons; shaded exons were deleted by targeting. The positive selection cassette was PGKpurobpA which contained puromycin N-acetyltransferase (Mielke et al., 1995, Trend. Genet. 11:258–259) expressed by the phosphoglycerate kinase 1 promoter (pgk-1; Adra et al., 1987, Gene 60:65–74) with a bovine growth hormone polyadenylation sequence (bpA; Pfarr et al., 1986, DNA 5:115–122). The negative selection cassette was MCltk (Mansour et al., 1988, Nature 336:348–352 ). b. Progeny of xrcc5$^{M1\pm}$ matings were screened by Southern blot analysis of tail DNA. BamHI-digested DNA was hybridized to a probe external to the deletion. The wild-type (+/+) genomic fragment is 12 kb while the targeted gene is 7.5 kb. Genotypes are indicated above each lane ($xrcc5^{M1+/-}$, +/-; $xrcc5^{M1-/-}$, -/-). c. Northern blot analysis of total RNA from genotyped embryonic fibroblast cells. RNA was hybridized to a cDNA probe (nucleotides 533–1393). The solid arrow indicates the wild-type (+/+) XRCC5 mRNA, which is 2.5 kb. The open arrow indicates the expected position of the mutant mRNA, which is expected to be 2.2 kb in length. RNA size markers are shown on the left side of the blot. β-actin hybridization control is in the bottom panel. d. RT-PCR of 5' and 3' regions of XRCC5 RNA from genotyped (shown above lanes) embryonic fibroblasts. Left panel: PCR products from indicated primer sets are shown in ethidium bromide (EtBr) stained agarose gels. Right panel: Southern blot of PCR products hybridized with indicated probes. RT-PCR for HPRT RNA was performed to ensure RNA integrity. Locations of primers and probes are shown above (a). Abbreviations: s, sense strand primer; as, antisense strand primer; tk, thymidine kinase gene (negative selection); puro, puromycin acetyltransferase gene (positive selection); restriction enzyme sites: B, BamHI; H, HindIII; S, SpeI.

FIGS. 2(A–C). Growth curve for control ($xrcc5^{M1+/-}$ and wild-type) and $xrcc5^{M1-/-}$ mice. Growth curve, inset for early time points. At embryonic day 14.5 the average weight for control and $xrcc5^{M1-/-}$ mice was 0.44 gm (n=15) and 0.27 gm (n=5), respectively. At embryonic day 17.5 the average weight for control and $xrcc5^{M1-/-}$ mice was 0.96 gm (n=7) and 0.70 gm (n=3), respectively. The heaviest $xrcc5^{M1-/-}$ mouse always weighed less than the lightest control mouse. After birth, 10 control mice and 6 $xrcc5^{M1-/-}$ mice were observed. Results for heterozygote and wild-type mice were combined because they were the same. DOB, date of birth; E, embryonic.

FIG. 3. Thymocytes from $xrcc5^{M1-/-}$ mice are arrested at an early stage of development. Thymocytes and splenic T cells from $xrcc5^{M1-/-}$ mice (-/-) and their control littermates (wild-type, +/+; $xrcc5^{M1+/-}$, +/-) were analyzed by flow cytometry. Cells were stained with fluorochrome-conjugated antibodies to CD4, CD8 and/or CD25; profiles shown are from day 19 mice; scid sample is from day 21. Numbers represent the percentage of total cells within the indicated region. Left panel, percentage for $CD4^+CD8^+$ thymocytes; middle panel, percentage $CD25^+$ cells from total thymocytes (note: gated $CD4^-CD8^-$ cells from wild-type and $xrcc5^{M1+/-}$ mice gave 23% and 18% $CD25^+$, respectively); right panel, percentage of $CD4^+$ splenic T cells. The $CD4^+$ splenic cells from wild-type and $xrcc5^{M1-/-}$ mice also stained brightly with antibodies to CD3 (not shown). Scattered $CD4^+$ populations observed in $xrcc5^{M1-/-}$ and scid mice were immature, $CD3^{lo}$, $TCR\alpha\beta^-$ cells; thus, the percentage is indicated in parenthesis. Note that the $CD8^+$ population in wild-type and $xrcc5^{M1+/-}$ mice is compressed against the x-axis.

FIG. 4. B cells from $xrcc5^{M1-/-}$ mice are arrested at an early stage of development. Bone marrow and spleens from $xrcc5^{M1-/-}$ mice (-/-) and their control littermates (wild-type, +/+; $xrcc5^{M1+/-}$, +/-) were analyzed for the presence of precursor and mature B cells. Cells were stained with conjugated antibodies to B220 and CD43 or IgM. Profiles are from the same mice shown in FIG. 3. Percentages are given for the indicated regions. Left panel, $B220^+CD43^-$ pre-B cells; middle and right panels, percentage of $B220^+$ cells that express surface IgM from bone marrow and spleen, respectively. Note that there are some $B220^{dull}$ $CD43^+$ cells in samples from $xrcc5^{M1-/-}$ and scid mice, representing the pro-B cell population.

FIGS. 5(A–E). Coding and signal joint formation are severely reduced in $xrcc5^{M1-/-}$ mice. a–d. Bone marrow and thymus DNA samples from $xrcc5^{M1-/-}$ mice (-/-) were subjected to semi-quantitative PCR analysis for coding joint formation. Titrations with DNA from wild-type (+/+) or $xrcc5^{M1+/-}$ (+/-) littermates were performed to estimate the abundance of coding joint formation in $xrcc5^{M1-/-}$ mice. Ig heavy chain $D_H$-$J_H$4 (a) and Ig $V_H$-$J_H$4 (b) coding joints are shown. Ig PCR products are derived from bone marrow DNA samples from individual $xrcc5^{M1-/-}$ mice, days 10, 16, and 2 months, (from left to right) and littermates (wild-type, day 10; $xrcc5^{M1+/-}$, day 16). Expected sizes of PCR products are approximately 120 bp ($D_H$-$J_H$4) and 360 bp ($V_H$7183-$J_H$4). T cell receptor Vβ8-Jβ2.6 (c) and Dδ2-Jδ1 (d) rearrangements from thymocyte DNA are shown. $xrcc5^{M1-/-}$ samples are pooled from two day 16 mice. Expected sizes of PCR products are 540 bp for Vβ8-Jβ2.5, 300 bp for Vβ8-Jβ2.6, 160 bp for Dδ2-Jδ1, and approximately 1 kb for the Dδ2-Jδ1 germ line product. 200 ng of DNA from $xrcc5^{M1-/-}$ mice and 100 ng from +/- and -/- littermates were used for TCR and Ig amplification except as noted. Scid bone marrow and thymocyte DNA samples (200 ng) were amplified at the same time for comparison. e. Signal joint formation is substantially reduced in $xrcc5^{M1-/-}$ mice. Circular PCR for T cell receptor Dδ2-Jδ1 signal joints is diagrammed, showing signal sequences (triangles) that have joined. The location of the internal oligonucleotide probe is indicated by an asterisk. The arrow on the blot indicates the expected size of PCR products containing a perfect signal joint. All lanes are from the same gel. The same 16 day old $xrcc5^{M1-/-}$ thymus DNA samples examined in (c) and (d) were used for this assay. Abbreviations. R, expected position of PCR product from rearrangements containing coding joints; GL, germ line; m, radiolabeled size standards (1 kb ladder, GIBCO-BRL); sj, signal joints. The sizes of relevant marker fragments are indicated.

FIGS. 6(A–E). Full-length signal ends are present in $xrcc5^{M1-/-}$ thymocytes. a. Schematic of LMPCR assay for the detection of signal ends. The signal sequence represented by a triangle is shown as a cleavage product prior to ligation of double-stranded primers (heavy lines). A full length signal end generates an ApaLI restriction site upon ligation. The location of the probe is indicated by the line terminating in an asterisk. Location of PCR primers are shown as arrows. b. Titration of Dδ2 signal ends from $xrcc5^{M1+/-}$ thymus DNA shows that LMPCR is semi-quantitative. Expected size of the PCR product is indicated. c,d. Dδ2 and Jδ1 signal ends, respectively in thymus DNA of two pooled day 16 samples of $xrcc5^{M1-/-}$ mice (-/-) and their $xrcc5^{M1+/-}$ littermates (+/-). A portion of each LMPCR sample was digested with ApaLI. LMPCR from uncut and cut samples were loaded in adjacent lanes. 200 ng of DNA were used in each PCR amplification (se, signal end). e. T4 DNA polymerase treatment fails to rescue non-blunt signal ends. Two different preparations of $xrcc5^{M1-/-}$ thymocyte DNA were examined in this experiment. 500 ng of DNA were used in each PCR amplification. Designated lanes (T4 pol.) contain samples that were treated with T4 DNA polymerase prior to ligation.

FIGS. 7(A–B). Accumulation of hairpin coding ends in $xrcc5^{M1-/-}$ thymocytes. a. Schematic of LMPCR to detect signal ends and hairpin coding ends. Treatment with mung bean nuclease (mbn) opens the hairpin coding ends, making them available for ligation. Ligation of double-stranded primers to signal ends and opened coding ends followed by PCR amplification generates products of 119 bp and 135 bp, respectively. The location of the probe is indicated by a line terminating in an asterisk. b. Assay for coding ends at Dδ2. Two pooled thymocyte DNA samples from day 16 xrcc5$^{M1-/-}$ mice (−/−) were treated with mung bean nuclease (mbn) followed by LMPCR. Thymocyte DNA from control littermates (wild-type, +/+; xrcc5$^{M1+/-}$, +/−) and from scid mice were treated in parallel and are shown for comparison (ce, coding end; se, signal end).

FIG. 8. Dose response curve for xrcc5$^{M1-/-}$, xrcc5$^{M1+/-}$ (heterozygote) and wild-type MEF exposed to 0, 1, 1.5, 2 and 3 Gy. The survival fraction (SF) was measured for cells derived from two xrcc5$^{M1-/-}$ embryos (average is presented) and cells derived from one heterozygote and one wild-type embryo.

FIGS. 9(A–C). Growth parameters for xrcc5$^{M1-/-}$, xrcc5$^{M1+/-}$ (heterozygote) and wild-type MEF and MSF. a. MEF growth curve. b. MSF growth curve. c. BrdU labeling of MEF. Control MEF, left panel; xrcc5$^{M1-/31}$ MEF, right panel.

FIGS. 10(A–C). Measurement of replicative senescence. Numbers observed in parenthesis. a, Colony size distribution for xrcc5$^{M1-/-}$ and control MEF and MSF. Results from heterozygote and wild-type cells were combined and averaged for control group. b, 3T3 analysis for xrcc5$^{M1-/-}$ and control MSF. The xrcc5$^{M1-/-}$ MSF stopped proliferating at passage 7. Two control MSF stopped proliferating at passage 20. Three control MSF spontaneously immortalized at passage 16–19 and were proliferating at a high rate (11=/−2× 10$^4$ cells/1.5 cm plate at passage 20). One control MSF spontaneously immortalized at passage 20 and were proliferating at a high rate (9.3×10$^4$ cells/1.5 cm plate by passage 21). An asterisk marks the point when spontaneous immortalization was observed and the numbers generated from these cells were no longer included in this figure. Results from heterozygote and wild-type cells were combined and averaged for control group. c, Morphology of control (1,3) and xrcc5$^{M1-/-}$ MEF (2,4). Cell suspension of passage 4 MEF (1,2). Crystal violet staining of MEF (3,4).

DETAILED DESCRIPTION OF THE INVENTION

Figure 1A:
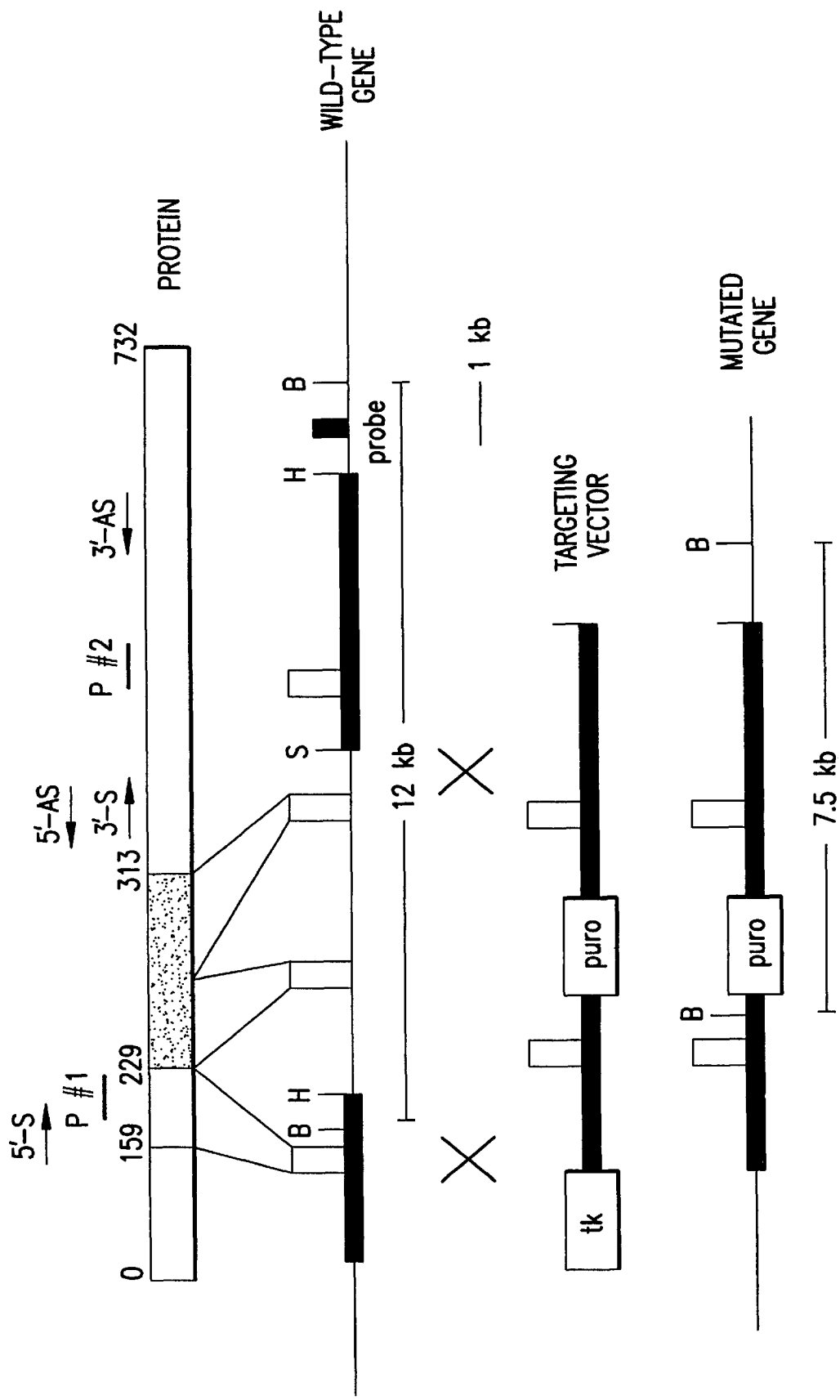
Figure 1B:
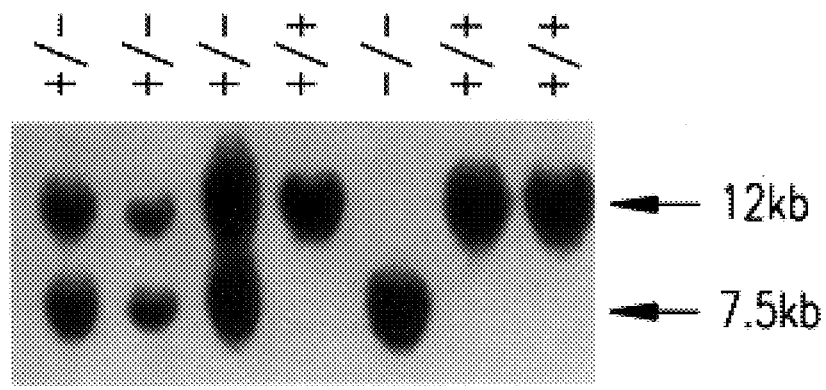
Figure 1C:
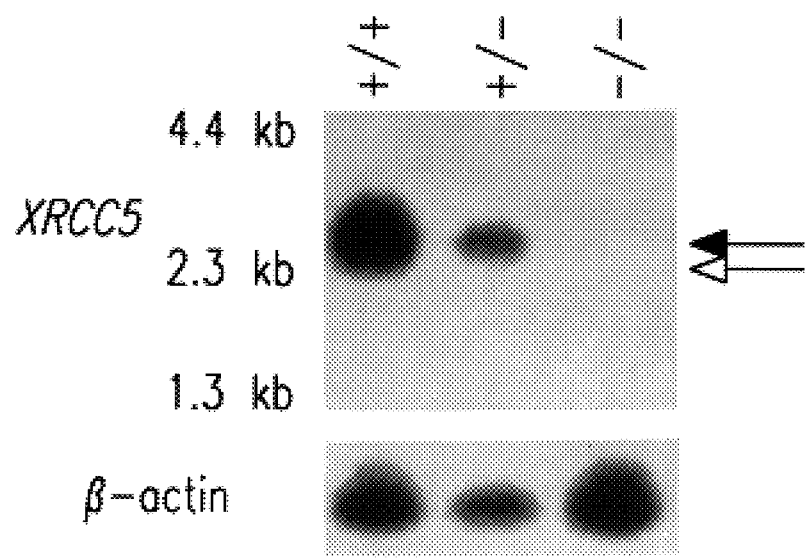

The present invention is directed to the production of Ku deficient cells, and Ku deficient non-human animals. The non-human transgenic animals contemplated by the present invention generally include any vertebrates, and preferably mammals, which encode a Ku, or XRCC5 homolog. Such nonhuman transgenic animals may include, for example, transgenic pigs, transgenic rats, transgenic rabbits, transgenic cattle, transgenic goats, and other transgenic animal species, particularly mammalian species, known in the art. Additionally, bovine, ovine, and porcine species, other members of the rodent family, e.g. rat, as well as rabbit and guinea pig and non-human primates, such as chimpanzee, may be used to practice the present invention. Particularly preferred animals are rats, rabbits, guinea pigs, and most preferably mice.

Preferred embodiments of the present invention include diploid mouse cells, mouse embryos, and mice that contain two chromosomal alleles of the XRCC5 gene, wherein at least one of the XRCC5 alleles contains a mutation such that said cell produces less than wild-type levels of Ku activity. Such Ku deficient animals and cells are deemed to be useful as, inter alia, disease models for the analysis and testing of therapeutic agents, and the effects of mutagenic stimuli such as radiation and chemical mutagens.

Replicative or cellular senescence is a process common to cells that leads to their terminal arrest and probably functions as a control against tumor formation and may reflect organismal aging (Campisi, 1996, Cell 84:497–500). Given that Ku deficient cells and animals apparently exhibit features of accelerated senescence, the presently described cells and animals are also deemed to be useful for the study of biological aging, and agents for retarding the same.

In particular, methods are contemplated for screening for conditions that rescue the proliferation and/or aging abnormalities of xrcc5$^{M1-/-}$ cells. Examples of such conditions include, but are not limited to, the presence of exogenously added protein or chemical factors, the over expression of transfected genes or endogenous genes, or the ectopic expression of transfected genes or endogenous genes, or the mutagenesis of genes and the like.

As used herein, xrcc5$^{M1}$ means that at least one of the two wild-type XRCC5 chromosomal alleles has been mutated such that less than wild-type levels of the Ku activity are produced. The extent of Ku86 deficiency can easily be measured by using standard molecular biology methods. For instance, one can measure for a deficiency in Ku86 messenger RNA levels by using reverse transcriptase mediated polymerase chain reaction (RT-PCR) (see FIG. 1). Thus, the term "Ku deficient" includes both homozygous XRCC5 mutant cells, as well as cells that are heterozygous for the XRCC5 mutant genotype, although a homozygous genotype is preferable. The term "Ku deficient" would also include both cells that are heterozygous mutants for the gene that encodes Ku70 and cells that are homozygous mutants for the gene that codes for Ku70. For the purposes of the present invention, a cell or animal that has been engineered to be Ku deficient shall generally express at least about 20 percent less Ku70 or Ku86 than a corresponding wild type cell or animal, and preferably at least about 50 percent less Ku 70 or Ku86 than wild type cells or animals, and more preferably at least about 90 percent less Ku70 or Ku86 than wild type cells or animals. In a particularly preferred embodiment, the Ku deficient cells or animals will produce less than 1.0 percent of the Ku70 or Ku86 protein found in wild type cells or animals, and in a specifically preferred embodiment the Ku deficient cells or animals will produce undetectable levels of full-length (wild type) XRCC5 transcript.

The mutation, or targeted disruption, in the XRCC5 gene may be engineered using any of a number of well established mutations that are well known in the art. Preferably, the mutation shall be a deletion mutation, although substitution mutations and/or insertion mutations are included within the scope of the present invention. Substitution mutations can be prepared by site directed mutagenesis, as described by (Hasty et al., 1991, Nature 350:243–246), that introduces a stop codon or other mutation near the 5' end of the XRCC5 gene such that abortive production of Ku86 protein results, or the production of a mutant protein which lacks Ku activity. Similarly, insertion mutations can be introduced within the XRCC5 gene taking advantage of the convenient restriction sites therein, such as any of the exonic restrictions sites or other sites which are easily identified by exonic sequencing of the XRCC5 gene and restriction mapping (FIG. 1), and the techniques described by Hasty et al., 1991, Molecular and Cellular Biology 11:4509–4517; Joyner et al., 1989, Nature 338:153–156. Another method of introducing an insertion or other mutation consists of infecting with a retrovirus which integrates in the XRCC5 locus, thereby creating a mutated xrcc5 allele as described by von Melchner et al., Genes and Development 6:919–927. However, the mutants of the present invention preferably lack part of the DNA sequence coding for Ku86 (i.e., deletion mutants) so that a defective xrcc5 allele is more likely made. An additional feature of deletion mutants are that, relative to the insertion mutants taught by von Melchner, there is a drastically reduced possibility of reversion to the non-mutant allele.

The coding region of the XRCC5 gene is approximately 2196 bp in size. For the purposes of the present invention, the nucleotides encoding the XRCC5 gene shall be numbered according to the gene bank accession #X66323, see SEQ ID NO:1. Deletion mutants can be produced by eliminating a DNA fragment from a coding region of the XRCC5 gene so that proper folding or substrate binding of the Ku86 protein is prevented. The size of the deletion may vary, but in general a larger deletion is preferable to a smaller deletion since the larger deletions are more likely to result in a deficiency in Ku activity. Typically, deletion mutations shall involve the excision of 1 base or up to essentially all of the bases of a given gene (including non-coding flanking regions). Alternatively, deleting a single base pair or two base pairs or any number of base pairs not divisible by 3 from the coding region would result in a frameshift mutation which would most likely be deleterious to making a functional Ku86 protein. In the latter instance, a truncated polypeptide may be produced because polypeptide synthesis is aborted due to a frame shift-induced stop codon. For a general review of mutagenesis and mutation see "An Introduction to Genetic Analysis", 4th edition, 1989 (D. Suzuki, A. Griffiths, J. Miller, and R. Lewontin, eds.), W. H. Freeman & Co., New York, N.Y.

Changing a single base pair (or multiple base pairs) in the coding region of the XRCC5 gene may also cause a mutation which, if resulting in an amino acid change, may alter the proper folding of the Ku86 protein and thereby create an Ku deficiency. A single amino acid change so generated could also alter the affinity of Ku86 for its substrate and thereby result in a deficiency of Ku activity. Another alternative would be to generate a deletion or other mutation in the non-coding region of the XRCC5 gene which affected the proper splicing of the XRCC5 messenger RNA. Such a mutation could effectively create a mutant XRCC5 transcript which was missing an entire exon or several exons as compared to the wild type XRCC5 message. Another alternative is to delete a non-coding regulatory region to decrease expression of the XRCC5 gene. The preferred size of the deletion is about several hundred nucleotides near the 5' end of the gene. Preferably, such a deletion would eliminate a number of nucleotides from the coding region not evenly divisible by 3, thereby creating a frameshift mutation as well. Alternatively, promoter sequences could be deleted or altered that would diminish transcription of the XRCC5 gene.

It is also possible to alter the expression of a given gene by altering the codon usage in the gene. Alterations of this sort preserve the amino acid sequence of the product while increasing or decreasing the levels of expression.

Antisense RNA transgenes may also be employed to partially or totally knock-out expression of specific genes (Helene., C. and Toulme, J., 1990, Biochimica Bioshys. Acta 1049:99; Pepin et al., 1991 Nature 355:725; Stout, J. and Caskey, T., 1990, Somat. Cell Mol. Genet. 16:369; Munir et al., 1990, Somat. Cell Mol. Genet. 16:383, each of which is incorporated herein by reference).

"Antisense polynucleotides" are polynucleotides that: (1) are complementary to all or part of a reference target sequence, such as the sequence of the XRCC5 gene, and specifically hybridize to a complementary target sequence, such as a chromosomal gene locus mRNA. Such complementary antisense polynucleotides may include nucleotide substitutions, additions, deletions, or transpositions, so long as specific hybridization to the relevant target sequence is retained as a functional property of the polynucleotide. Complementary antisense polynucleotides include antisense RNA which can hybridize specifically to individual mRNA species and hinder or prevent transcription and/or RNA processing of the mRNA species and/or translation of the encoded polypeptide (Ching et al., 1989, Proc. Natl. Acad. Sci. U.S.A. 86:10006–10010; Broder et al., Ann. Int. Med. 113:604–618; Loreau et al., 1990, FEBS Letters 274:53–56; Holcenberg et al., WO91/11535; WO91/09865; WO91/04753; WO90/13641; and EP 386563, each of which is incorporated herein by reference). An antisense sequence is a polynucleotide sequence of at least about 15 contiguous nucleotides in length, typically at least 20 to 30 nucleotides in length, and preferably more than about 30 nucleotides in length that is substantially complementary to a target gene sequence, or sequences, in a cell. In some embodiments, antisense sequences may have substitutions, additions, or deletions as compared to the complementary target sequence but as long as specific hybridization is retained, the polynucleotide will generally function as an antisense inhibitor of gene expression.

For the purposes of the present invention, the antisense sequence is complementary to an endogenous XRCC5 target gene sequence. In some cases, sense sequences corresponding to the XRCC5 target region sequence may function to suppress expression, particularly by interfering with transcription. Alternatively, an antisense polynucleotide will generally suppress XRCC5 expression at a post transcriptional level.

Given that antisense polynucleotides inhibit the production of the polypeptide(s) in cells, they may further alter a non-human transgenic animal's capacity to produce Ku.

Antisense polynucleotides may be produced from a heterologous expression cassette inserted into transgenic pluripotent embryonic stem cells which may subsequently be used to generate the presently described Ku deficient animals.

The gene modified animal cells of the present invention can be prepared by any of several techniques that are well established in the art. In particular, techniques conceptually similar to those taught in U.S. Pat. No. 5,464,764 issued to Capecchi and Thomas on Nov. 7, 1995, herein incorporated by reference, may be used. In general, Ku defective cells may be engineered using the following steps:

(1) Constructing a targeting vector comprising a cloning vector and a DNA fragment containing at least one positively selectable marker gene (positive selection marker), flanked by two regions of the mouse XRCC5 gene or genomic locus which are in the same 5' to 3' orientation to one another (referred to as the regions of homology);

(2) Included in the targeting vector is a negatively selectable marker gene (negative selection marker) adjacent to one of the regions of homology. This negatively selectable marker may increase the likelihood of recovering the desired homologous recombination event (deleting a portion of the XRCC5 gene) but it is not required;

(3) Transfecting XRCC5$^{+/+}$ mouse cells with the targeting vector of step (2);

(4) Selecting the transfected cells from step 3 for the marker(s) on the vector; and (5) Screening for Ku deficient mouse cells from those cells in step (4) which are found to contain or express said positive selection marker(s), and not express said negative selection marker(s).

The precise XRCC5 gene or gene locus sequences which must be present in the targeting vector of step (1) will depend on the sequences chosen for the deletion, and (2) the restriction nucleases to be employed in the engineering of the deletion mutant.

The specific regions of homology required in step (1) depend on the specifics of the deletion in the targeting vector. In general, the homology regions used in the targeting vector will preferably comprise at least about 400 bp, though longer or shorter regions may also be used. In general it is preferable to use homology regions of approximately 1.5 kb or greater to insure a high degree of targeting efficiency. The targeting vector described in detail in FIG. 1, the 5' and 3' homology regions on both sides of the deletion were 3 kb and 4.4 kb, respectively.

The size of the deletion may also vary and depends on the regions of homology used in the targeting vector. Since non-contiguous regions of homology are used in the deletion targeting vector, that region in the wild-type allele which is located between the regions of homology constitutes the region to be deleted after homologous recombination with the targeting vector. Although, the region deleted in the specific examples is approximately 6.0 kb in length, that particular size is not critical and either more or less may be deleted from the locus while still effecting Ku deficiency. Generally, it is preferable to delete at least a portion of an exon of the XRCC5 gene, or an entire exon, which results in a correspondingly mutated XRCC5 messenger RNA.

The particular positive and negative selection markers employed in the present invention are not critical to the practice of the invention. Examples of preferred positive and negative selection markers are listed in Table 1. The positive selectable marker should be located between the regions of homology and the negative marker, if one is used, should be outside the regions of homology, either 5' or 3' to those regions as shown in FIG. 1a. The regions of homology should generally be present in the vector in the same 5' to 3' orientation relative to one another. Conversely, the relative orientations of the positive and negative selectable markers are not critical. In fact, it is not really necessary to include a negative selectable marker, even though the presence of the negative marker may improve selection for targeted clones.

Preferably, the positive selectable marker is expressed in the cells that are targeted for gene modification. Positive and/or negative selection markers are deemed to be functional in the transfected cells if the DNA sequences encoding the selectable markers are capable of conferring either a positive or negative phenotypic selection characteristic to cells expressing the sequences. In general, the marker will be operably linked to a regulatory sequence that mediates the expression of the marker. A nucleic acid marker is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous.

Additionally, the means by which the positive selectable marker gene is made functional is not critical to the present invention. Positive selection is accomplished by exposing the cells to an appropriate agent which kills or otherwise selects against cells that do not contain or express an integrated positive selection marker. A representative, but not limiting, list of such agents is presented in Table 1. The positive selectable marker gene may have a promoter driving its expression or it may be driven by the juxtaposition of transcriptional elements at the target locus with the positive selectable marker. The latter gene organization requires that the transcriptional elements are active in the transfected cells.

In addition to a positive selection marker, the mutation engineered into the targeting vector may contain DNA sequence, e.g., an oligonucleotide linker, between the regions of XRCC5 gene homology in place of the deleted XRCC5 DNA. The oligonucleotide linker is generally about 8–10 nucleotides in length, but can be longer, e.g. about 50 nucleotides, or shorter, e.g. 4, 5 or 7 nucleotides. The preferred length of the oligonucleotide linker is about 20 to 40 nucleotides in length. The DNA sequence of the oligonucleotide linker is not critical.

The method of inserting the oligonucleotide between the regions of homology in the targeting vector DNA will depend upon the type of oligonucleotide linker used. Palindromic double stranded linkers containing one or more restriction nuclease sites in the oligonucleotide sequence (New England Biolabs) may be inserted by well known procedures (Maniatis et al., 1982, *Molecular Cloning*, Cold Spring Harbor Laboratory, Cold Spring Harbor Press, New York)

Oligonucleotide linkers may also be inserted into deletions in plasmid DNA by tailing ends with complementary homopolymers using terminal transferase (Maniatis et al., supra), or a single stranded oligonucleotide linker may be inserted into a deletion in a plasmid by bridging, through annealing of an oligonucleotide containing ends complementary, to a cleaved plasmid's 3'-recessed and 3'-protruding cohesive ends, followed by filling-in the gap complementary to the oligonucleotide sequence with DNA polymerase (Klenow fragment). After subsequent ligation with T4 DNA ligase, closed circular DNA molecules can be regenerated.

Alternatively, site-directed mutagenesis may be used to simultaneously construct a specific deletion and insert a linker sequence by using a single stranded oligonucleotide to "loop-out" the desired region of the target gene (Krogstad and Champoux (1990) J. Virol. 64(6):2796–2801, herein incorporated by reference).

If the targeting vector is designed such that the deleted region interrupts an exon, by the judicious choice of oligonucleotide linker length and sequence, frame shift mutations and/or stop codons may be produced in the XRCC5 gene in addition to the deletion within the XRCC5 gene.

The mutation engineered in the targeting vector may contain DNA sequences between the regions of XRCC5 gene homology in addition to the positive selection marker, for example, splice acceptor sequences. Such sequences have been shown to result in aberrant, and hence nonfunctional, mRNAs.

The DNA sequences used in the regions of homology should generally be derived from XRCC5 gene sequence, sequences that flank the XRCC5 gene locus, or a combination thereof. Where an XRCC5 knockout mouse is desired, the strain of mouse from which the XRCC5 DNA is derived is not critical, but preferably the gene should be from the same as the strain of mouse as the cells targeted for gene transfer. Using DNA (in the regions of homology) that is isogenic to the target cells will generally enhance the efficiency of gene targeting. The regions of homology may be derived from genomic libraries of mouse DNA which may be cloned into a variety of cloning vectors such as lambda phage vectors, cosmid vectors, plasmid vectors, p1 phage vectors, yeast artificial chromosome vectors, and the like. Regions of homology to be incorporated into the targeting vector may also be derived from genomic DNA using polymerase chain reaction (PCR). The PCR method would generally use the published sequence of the XRCC5 gene. Regions of homology so derived could be subcloned directly into the targeting vector. Alternatively, the regions of homology may be derived from an appropriate cDNA library.

Any of a wide variety of cloning vectors may be used to construct the XRCC5 targeting vectors of the present invention. Examples of such cloning vectors include, but are not limited to, pBR322 and pBR322-based vectors (Sekiguchi, 1983, Gene 21:267), pMB9, pBR325, pKH47 (Bethesda Research Laboratories), pBR328, pHC79, phage Charon 28 (Bethesda Research Laboratories, Boehringer Mannheim Biochemicals), pKB11, pKSV-10 (P-L Biochemicals), and oligonucleotide (dg)-tailed pBR322 (Bethesda Research Laboratories), pBluescript or similar plasmids (Stratagene), puc19 or related plasmids (New England Biolabs), and the like.

The targeting vector will generally comprise two regions of XRCC5 homology separated by a positive selectable marker, and, optionally, a flanking negative selectable marker that is not critical as long as the cloning vector contains a gene expressing a selectable trait, e.g. drug resistance. The targeting vector may also be cloned into other cloning vectors such as lambda phage vectors, cosmid vectors, plasmid vectors, p1 phage vectors, yeast artificial chromosome vectors, and the like.

Another option is to prepare the components of the targeting vector synthetically by PCR and simply ligating each component such that the positive selectable marker is placed between the regions of homology, and the homology regions are place in the proper orientation relative to one another.

Other cloning vectors containing unique cloning sites which are useful in the present invention may be selected upon evaluation of restriction nucleases other than SalI and HindIII (used for the 5' region of homology) and SpeI and HindIII (used for the 3' region of homology) which were used with the vector DV6.0 to construct the specifically exemplified targeting vector (see FIG. 1).

Any of a variety of additional restriction nucleases may be employed to produce fragments containing the mouse XRCC5 gene. Thus, the mouse XRCC5 gene restriction map provides guidance as to which of a wide variety of cloning vectors may be used to conveniently practice the present invention. In fact, many combinations of restriction endonucleases could be used to generate an XRCC5 targeting vector to mutate the XRCC5 gene.

These regions of homology may be cloned into any of a large number of commercially available plasmids such as, but not limited to, the pBluescript series (Stratagene), the pUC series (New England Biolabs), or the pGEM series (Promega).

The specific host employed for growing the targeting vectors of the present invention is not critical, but the host will preferable have a functional hsd modification system. Examples of such hosts include E. coli K12 RR1 (Bolivar et al., 1977, Gene 2:95); E. coli K12 HB101 (ATCC No. 33694); E. coli MM21 (ATCC No. 336780); and E. coli DH1 (ATCC No. 33849). The preferred host in the present invention is E. coli strain DH5α (Life Technologies). Similarly, alternative vector/cloning systems could be employed such as targeting vectors which grow in E. coli or Saccharomyces cerevisiae, or both, or plasmid vectors which grow in B. subtilus (Ure et al., 1983, Methods in Enzymology, "Recombinant DNA", vol. 101, Part C, Academic Press, New York).

The specific mouse cell which is mutated in the present invention is not critical; however, it is preferably a precursor cell or at least pluripotent cell. The term precursor means that the pluripotent cell is a precursor of the desired transfected pluripotent cell of the present invention. Using established techniques, pluripotent cells may be cultured in vivo to form a mutant animals (Evans et al., 1981, Nature 292:292–156). Specific examples of mouse cells that may be employed in the present invention include, but are not limited to, embryonic stem (ES) cells (preferably primary isolates of ES cells), such as AB 1 or AB 2.1. AB 2.1, an hprt$^-$ cell line, AB 1, an hprt$^+$ cell line. Other selectable markers such as those exemplified in Table I may be used in other stem cell lines.

Primary isolates of ES cells may be obtained directly from embryos, essentially as described for the EK.CCE cell line or for ES cells in general. The particular embryonic stem cell employed in the present invention is not critical.

ES cells are preferably cultured on stromal cells, e.g., STO cells and/or primary embryonic fibroblast cells as described by Robertson, 1987, In "Teratocarcinomas and embryonic stem cells: a practical approach", E. J. Robertson, ed. (Oxford: IRL Press), pp. 71–112. The stromal (and/or fibroblast) cells serve to reduce the clonal outgrowth of abnormal ES cells.

In order to obtain the Ku deficient mice of the present invention, the mutant embryonic stems cells are injected into mouse blastocysts as described by Bradley, 1987, In "Teratocarcinomas and embryonic stem cells: a practical approach", E. Robertson, ed. (Oxford: IRL Press), pp. 113–151.

The particular mouse blastocysts employed in the present invention are not critical. Examples of such blastocysts include those derived from C57BL6 mice, C57BL6Albino, Swiss outbred, CFLP, MFI, and the like.

Mice heterozygous for the xrcc5$^{M1}$ mutant allele generated from the injected blastocyst can be screened for mutations in the XRCC5 gene, e.g., by Southern blotting using DNA probes for said mutation (FIG. 1), or by PCR. For example, in Example 4 below, Southern blot using a probe 3' to the mutated locus identified mice heterozygous for the engineered mutation by detecting the presence of a 12 kb mutant DNA fragment, and a 7.5 kb wild type DNA fragment (FIGS. 1a, b).

The mutant mice of the present invention may be intercrossed to obtain embryos homozygous for the mutation in the XRCC5 gene, and/or may be crossed with other mice strains to transfer the xrcc5$^{M1}$ mutation into these other strains. For example, as described in Example 4 below, Southern blots using a probe 3' to the mutated locus identified mice homozygous for the engineered mutation by only detecting the presence of a 7.5 kb mutant DNA fragment, and not detecting the 12 kb wild type DNA fragment (FIGS. 1a, b).

The examples below are provided to illustrate the subject invention. Given the level of skill in the art, one may be expected to modify any of the above or following disclosure to produce insubstantial differences from the specifically described features of the present invention. As such, the following examples are provided by way of illustration and are not included for the purpose of limiting the invention in any way whatsoever.

EXAMPLES

Embryonic stem cells were manipulated essentially as described by published procedures (Teratocarcinomas and embryonic stem cells: a practical approach, E. J. Robertson, ed., IRL Press, Washington, D.C., 1987; Zjilstra et al., 1989, Nature 342:435–438; and Schwartzberg et al., 1989, Science 246:799–803, each of which is herein incorporated by reference).

DNA cloning procedures were carried out essentially as described in J. Sambrook, et al. in Molecular Cloning: A Laboratory Manual, 2d ed., 1989, and periodic updates thereof, Cold Spring Harbor Laboratory Press, Cold Spring Harbor, N.Y., which is incorporated herein by reference.

Oligonucleotides were synthesized on an Applied Bio Systems oligonucleotide synthesizer according to specifications provided by the manufacturer.

6.1. Cloning of the Mouse XRCC5 Gene

The mouse XRCC5 gene was cloned from a mouse 129-strain genomic library. More specifically, a fragment of the XRCC5 gene was obtained using oligonucleotides based on nucleotide sequence (gene bank accession #X66323, see SEQ ID NO:1) information and reverse transcriptase mediated polymerase chain reaction on RNA from mouse cells. The fragment of the mouse gene so obtained was subcloned into a plasmid vector pBluescript SK+ (Stratagene). A radiolabeled probe was made using the subclone of the XRCC5 gene, and the probe was used to screen a mouse 129-strain genomic lambda phage library to identify phage containing the mouse XRCC5 gene. Three positive phage were isolated and grown, and restriction mapping was performed on the DNA inserts by standard techniques to produce a restriction map of the XRCC5 genomic locus (see FIG. 1a). Based on the restriction map data, putative exons were identified by hybridization and selected exonic sequencing was performed.

6.2. Construction of Targeting Vector

To generate Ku-deficient mice, a targeting vector was first constructed. This vector contained 3.0 kb of DNA homologous to the 5' end of the mouse XRCC5 gene, and 4.4 kb of DNA homologous to the 3' end of the mouse XRCC5 gene. This vector also contained a marker for positive selection (the puromycin cassette), and a marker for negative selection (the thymidine kinase gene; Mansour et al., 1988).

More specifically, based on the restriction map data, 5' and 3' homology regions were selected. The 5' homology region used was located near the 5' end of the XRCC5 genomic locus and was isolated by a SalI(engineered)/HindIII digest (FIG. 1a) which released an approximately 3.0 kb DNA fragment.

The 3' homology region was isolated by a SpeI/HindIII digest which produced a DNA fragment of approximately 4.4 kb (FIG. 1a). The positive selectable marker used was the puromycin cassette.

To prepare the positive selection targeting vector, the 6.0 kb HindIII/SpeI genomic fragment (which contains coding nucleotides 701–964) was removed and replaced with the positive selectable marker cassette. To prepare a positive-negative selection targeting vector, the negatively selectable thymidine kinase (tk) gene was added exterior to the 3' homology region. The unique SalI site was then used to cut the vector prior to transfection (FIG. 1).

6.3. Transfection of Mouse Embryonic Stem Cells

Homologous recombination of the targeting vector with the XRCC5 genomic locus was effected in mouse embryonic stem cells (See FIG. 1). More specifically, 10 μg of the positive-negative targeting vector described in section 6.2 was transfected into 1×10$^7$ 129 mouse strain embryonic stem cells, and the resulting cells were grown in the presence of puromycin to select for cells that had successfully incorporated with the targeting construct. Negative selection against the tk gene was also applied using the drug FIAU so as to enhance selection for those cells which had undergone a homologous recombination event at the XRCC5 locus. Surviving colonies were screened by mini-Southern, as described by Ramirez-Solis (1992, Anal. Biochem. 201:331–336) using a labeled DNA fragment from the XRCC5 locus which was 3' to the region of homology of the targeting vector as a probe for detecting the double reciprocal homologous recombination event between the targeting vector, and the XRCC5 locus in the chromosome of the ES cell (FIGS. 1a, b).

ES cell genomic DNA for the minisouthern was digested with restriction enzyme BamHI. The desired recombination event was detected using the 5' probe which revealed a mutant allele of 7.5 kb as compared to the wild type allele of 12 kb. Many positive ES cells clones were identified that contained the desired gene replacement event (i.e., an approximately 6.0 kb genomic deletion).

6.4. Generation of Ku-deficient Mice

Two ES cell clones obtained as described in section 6.3. were injected into C57BL6 Albino host blastocysts as has been described (Bradley, 1987). Injected blastocysts were implanted into pseudopregnant females and chimeric offspring were born as demonstrated by the mixture of agouti and albino coat colors (agouti contribution from the ES cell line, and albino from the wild-type host embryos, see Bradley, 1987). Chimeric male mice were mated to wild-type C57BL6 Albino females and agouti pups were born indicating successful germ line transmission of the ES cell component of the chimeric mouse, resulting in C57BL6 Albino/129 hybrids (referred to as C567BL6/129 hybrids). At three weeks of age, the offspring from the chimeric crosses were screened for the mutant xrcc5$^{M1}$ allele as described below.

Genomic DNA was isolated from the resulting mice. Then 10 μg of the resulting genomic DNA was digested with BamHI, and subjected to Southern blot analysis using the 3' probe essentially as described above for the minisoutherns (FIG. 1b). Two ES cell clones transmitted the desired mutant allele through the germ line as evidenced by the deletion of 6.0 kb of genomic sequence, and the elimination of 263 bp of coding sequence from the mouse XRCC5 gene.

A male and female mouse were also identified as heterozygous for the mutant allele (xrcc5$^{M1}$), and these mice were intercrossed. Genomic DNA was isolated from the resulting progeny and 10 μg of the genomic DNA was digested with BamHI, and subjected to Southern blot analysis, using the 3' XRCC5 probe as described above. A single 12 kb band indicated a homozygous wild-type animal (+/+) animal, a single 7.5 kb band indicated an animal homozygous for the targeted mutant allele (xrcc5$^{M1}$/xrcc5$^{M1}$ or xrcc5$^{M1-/-}$ or mutant). The presence of both bands indicated a heterozygous animal (xrcc5$^{M1}$/+ or xrcc5$^{M1+/-}$).

Several mating pairs of xrcc5$^{M1+/-}$ mice were intercrossed to obtain xrcc5$^{M1-/-}$ mice. A Mendelian pattern of inheritance was observed.

6.5. The xrcc5$^{M1}$ mutation is most likely null

Consequences of the xrcc5$^{M1}$ mutation on XRCC5 transcript levels was determined by Northern analysis on mRNA isolated from murine embryonic fibroblasts (MEF) derived from control and mutant (day 14.5) embryos (FIG. 1c). β-actin transcript levels were also measured as controls for mRNA loading, and were detected in control and mutant embryos. XRCC5 mRNA was detected in control but not mutant MEF.

Figure 1D:
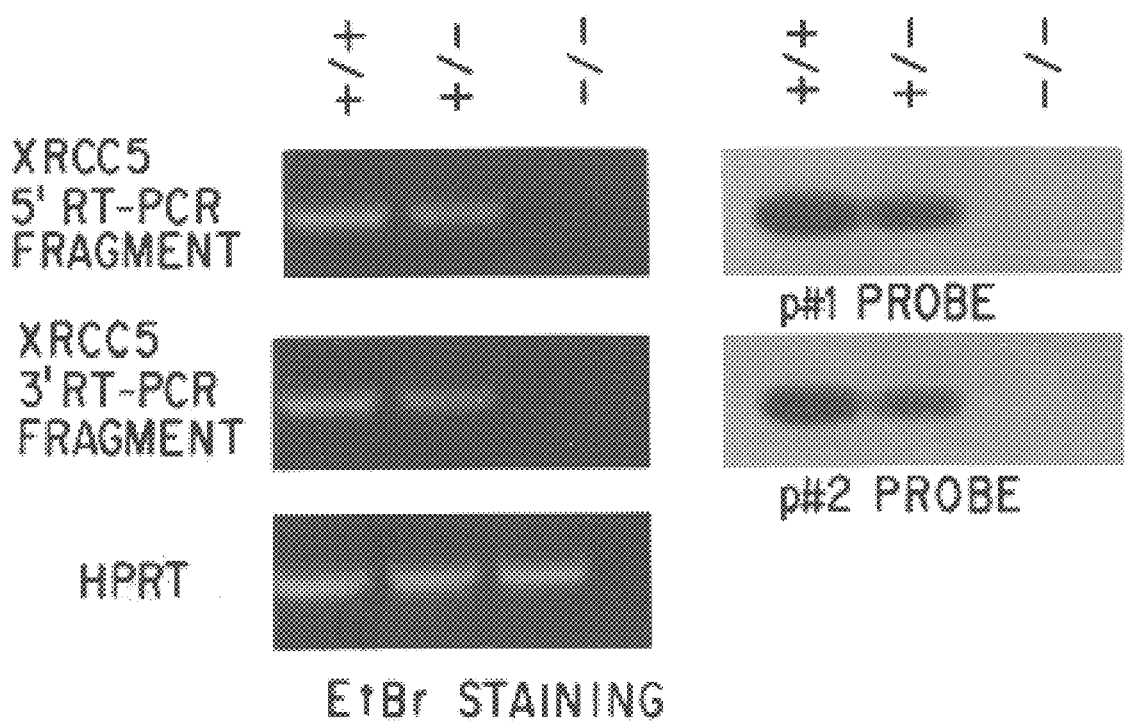
Figure 2A:
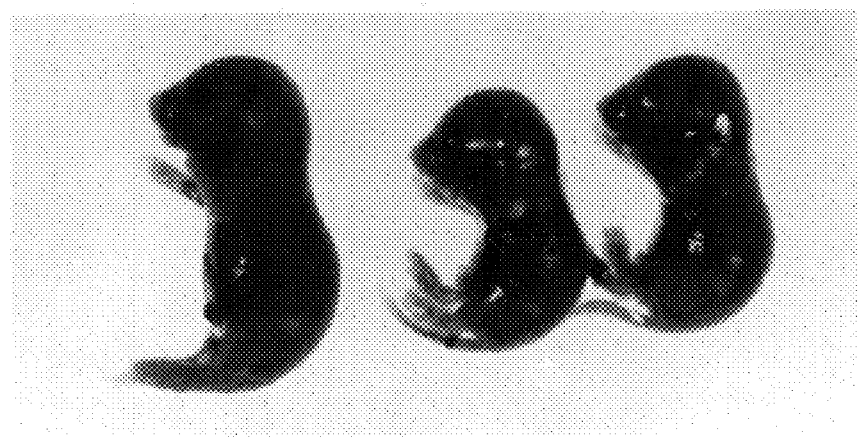
Figure 2B:
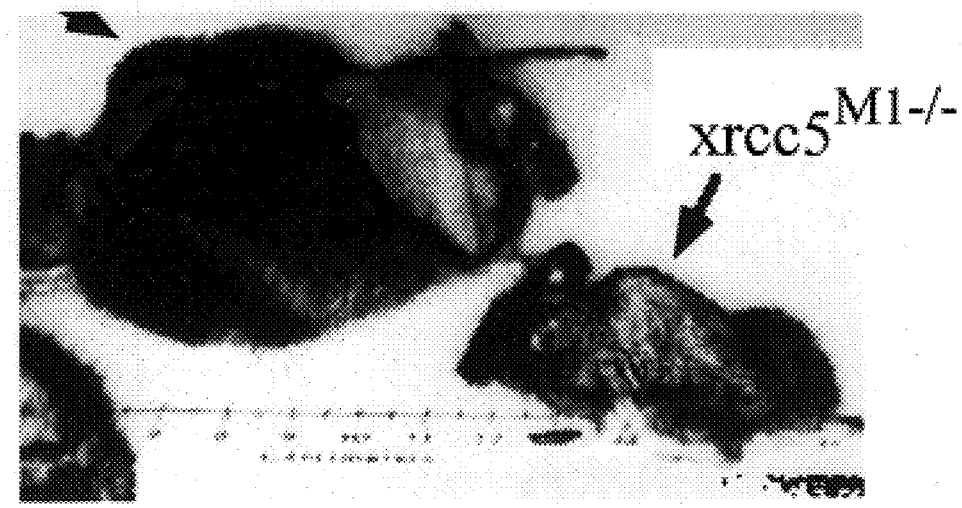
Figure 2C:
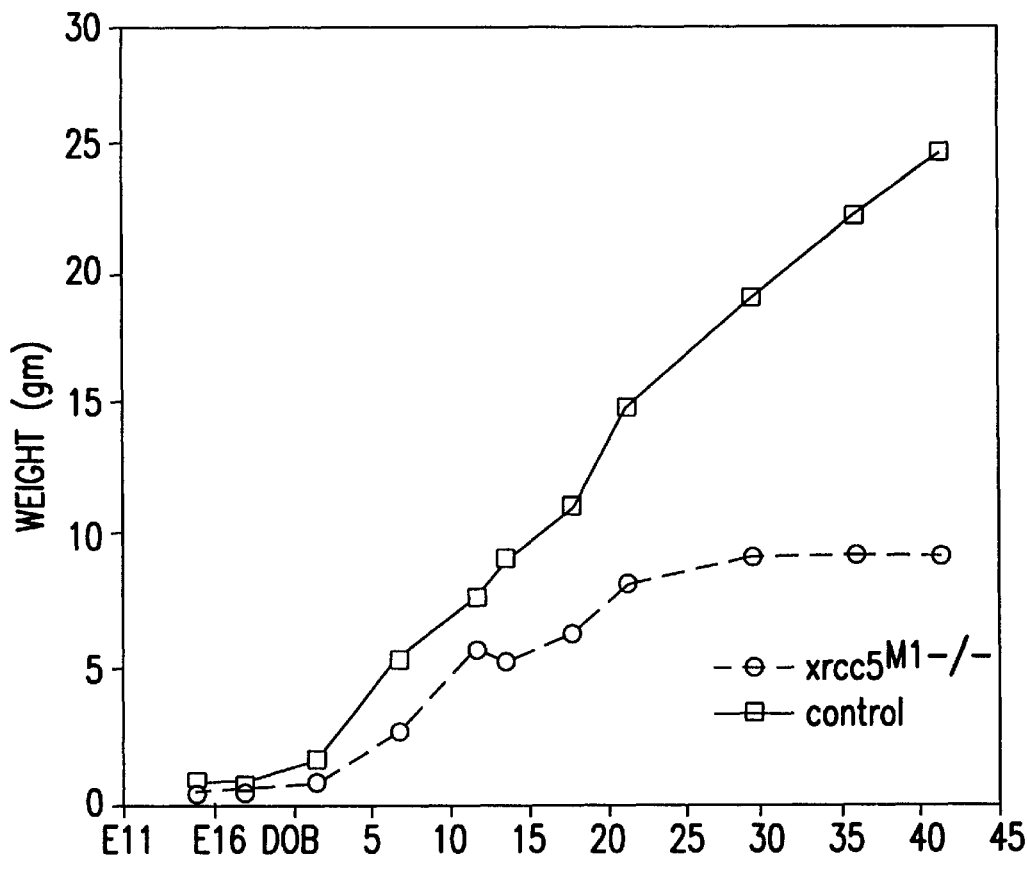
Figure 2D:
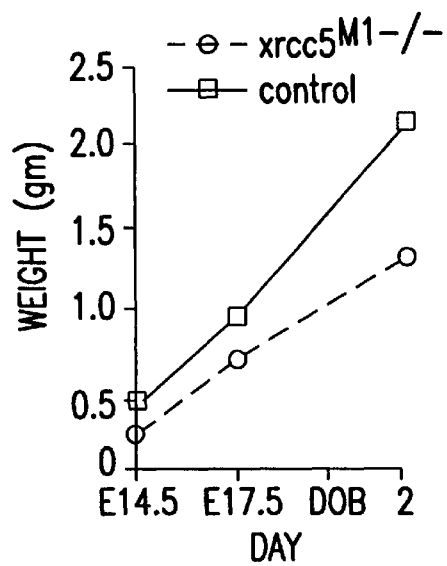

The xrcc5$^{M1}$ mutation's effect on XRCC5 transcript levels was determined by reverse transcriptase mediated polymerase chain reaction (RT-PCR) on mRNA isolated from murine embryonic fibroblasts (MEF) derived from control and mutant day 14.5 embryos (FIG. 1d). GAPDH transcript levels were measured to control for mRNA loading and were detected in control and mutant embryos. XRCC5 mRNA was detected in control but not mutant MEF, even after hybridization with an internal oligonucleotide probe. The out-of-frame deletion and the lack of XRCC5 mRNA make it likely the xrcc5$^{M1}$ mutation was null.

6.6. xrcc5$^{M1}$ Mice are Small

Timed heterozygous matings were performed with xrcc5$^{M1+/-}$ females and xrcc5$^{M1+/-}$ males. The most obvious abnormality observed in xrcc5$^{M1-/-}$ embryos or mice, was small size (FIG. 2) which was not observed in scid mice which indicates that Ku may function independently of DNA-PK$_{cs}$. No obvious defects were observed on histological sections from the brain, lung, heart, kidney, liver, stomach, small intestine, large intestine, pancreas and ovary from six mutant mice which were indicative of inefficient weight gain (data not shown). Histological sections of the thymus, spleen and lymph nodes revealed severe reduction in mature lymphocytes; however, this should not decrease growth, since scid mice grow normally (Table 2).

6.7. Mature T and B Cells Fail to Develop in xrcc5$^{M1}$ Mutant Mice

Because Ku86 has been implicated in V(D)J recombination in cultured fibroblast cells, we examined mutant mice for effects on development of the immune system. Normal development of T and B cells is a highly ordered process dependent on the successful rearrangement of antigen receptor gene segments. Rearrangement at the TCRβ locus is initiated in precursor T cells at the CD4$^-$ CD8$^-$ CD25$^+$ stage of development. Successful rearrangement of the β chain allows developmental progression to the CD4$^+$ CD8$^+$ CD25$^-$ stage, where TCRα rearrangement occurs.

Figure 3:
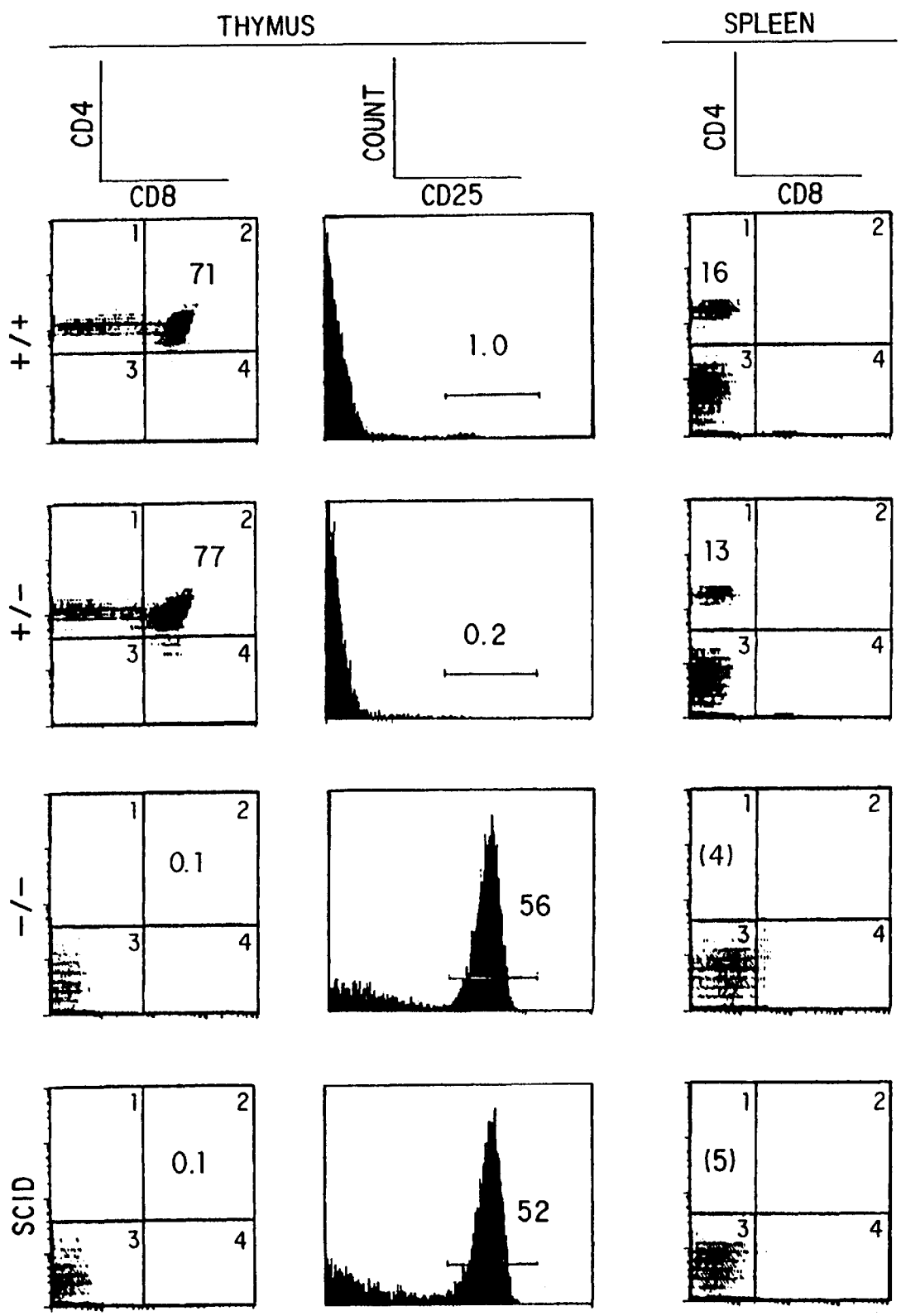

We examined twenty-four Ku-deficient mice and their littermates, varying in age from newborn to 10 weeks. Thymocytes from Ku-deficient mice were arrested at the CD4$^-$ CD8$^-$ CD25$^+$ stage as shown by flow cytometry from a representative animal in FIG. 3. Over 90% of the Ku-deficient thymocytes were CD4$^-$ CD8$^-$ in comparison to thymocytes from wild-type or heterozygous mice which comprised only 5–10% CD4$^-$ CD8$^-$ cells. The majority of thymocytes from wild-type or heterozygous mice are at more mature developmental stages. Over 50% of the CD4$^-$ CD8$^-$ thymocytes are CD25$^+$ in the mutant mice; further phenotypic analysis revealed thymocytes from Ku-deficient mice to be CD3$^{lo}$ TCRαβ$^-$ and TCRγδ$^-$.

The early developmental block in Ku-deficient thymocytes results in a profoundly hypocellular thymus, similar to a scid thymus, with 50- to 170-fold fewer cells than in wild-type or heterozygous littermates (Table 2). Lymph nodes were also hypocellular and difficult to recover, suggesting that the defect in thymocyte development is reflected in the periphery. Spleen, lymph nodes, and blood were assayed for the detection of mature TCRαβ$^+$ cells which express high levels of CD3 and either CD4 or CD8. Distinct, mature T cell populations, which are easily discernible in the periphery of wild-type or heterozygous mice, were not detected by flow cytometry in Ku-deficient mice (see spleen, FIG. 3; lymph node and peripheral blood lymphocyte data not shown).

Occasionally, rare CD4$^+$ cells were detected in the spleen or lymph nodes of Ku-deficient mice (FIG. 4); however, these cells were immature with a CD3$^{lo}$ TCRαβ$^-$ phenotype.

Figure 4:
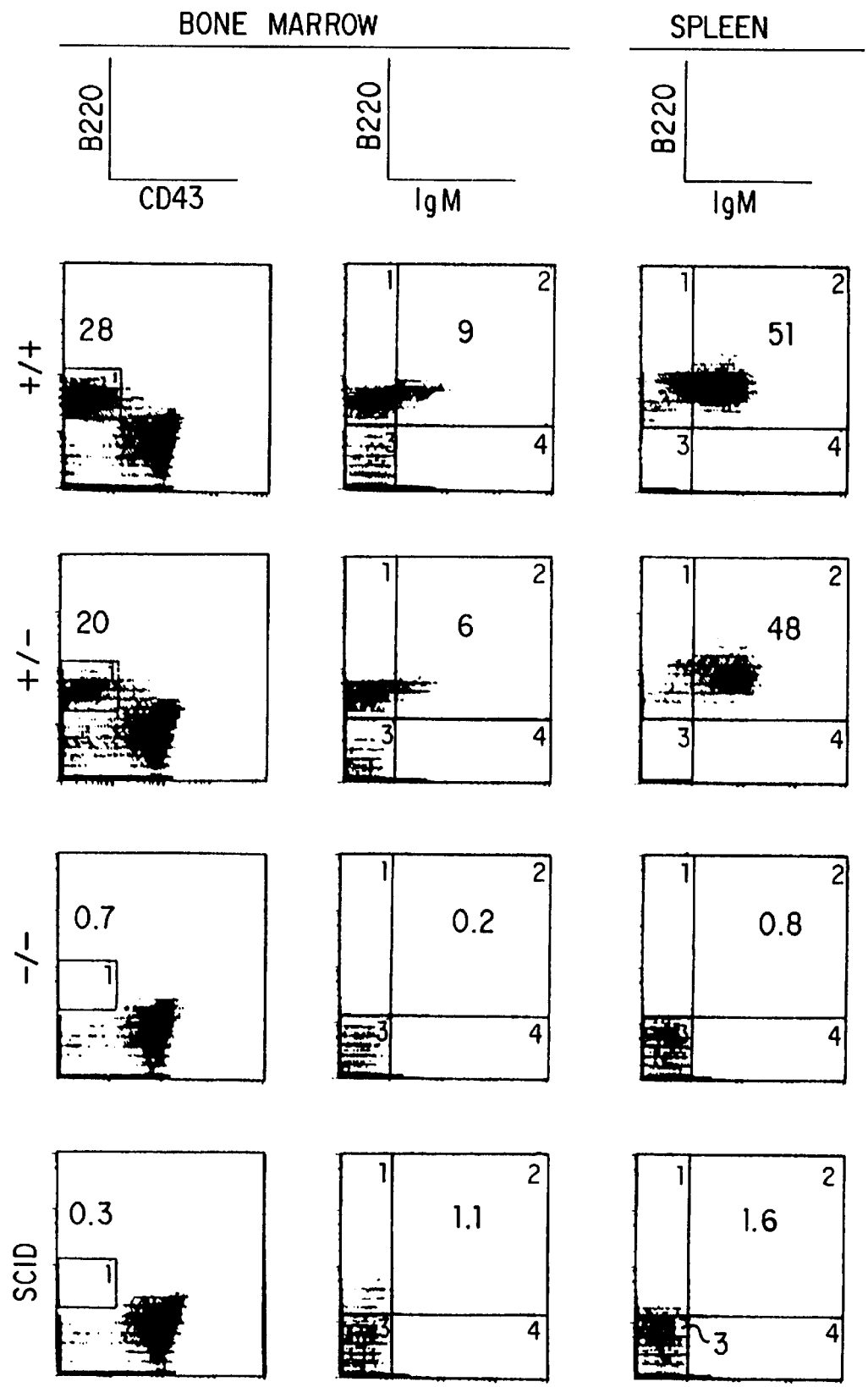

Analysis of the B cell compartment in Ku-mutant mice also showed developmental arrest at an early stage. Normally, immunoglobulin heavy chain rearrangement is initiated in pro-B cells (B220$^{dull}$ CD43$^+$) in the bone marrow. Once a functional heavy chain has been expressed, the cells progress to the pre-B cell stage (B220$^+$ CD43$^-$) where Ig light chain rearrangement occurs. B cell development in Ku-deficient mice is arrested at the B220$^{dull}$ CD43$^+$ stage as shown in FIG. 4. We estimate that the number of cells arrested at this stage in Ku-deficient mice is similar to that in scid bone marrow, with percentages ranging from 5–10% of total bone marrow cells in both mutant animals. No distinct B220$^+$CD43$^-$ population was identified in Ku-deficient mice, and cells expressing surface IgM were not detected. Mature B cells from Ku-deficient mice were not apparent in the spleen (FIG. 4), lymph nodes, or peripheral blood (not shown). In summary, the immunophenotype of Ku-deficient mice is similar to that of scid mice (Bosma et al., 1983, Nature 301:527–530; Schuler et al., 1986, Cell 46:963–972), suggesting a severe impairment in the assembly of functional TCR and Ig molecules.

6.8. impaired formation of coding joints

Figure 5A:
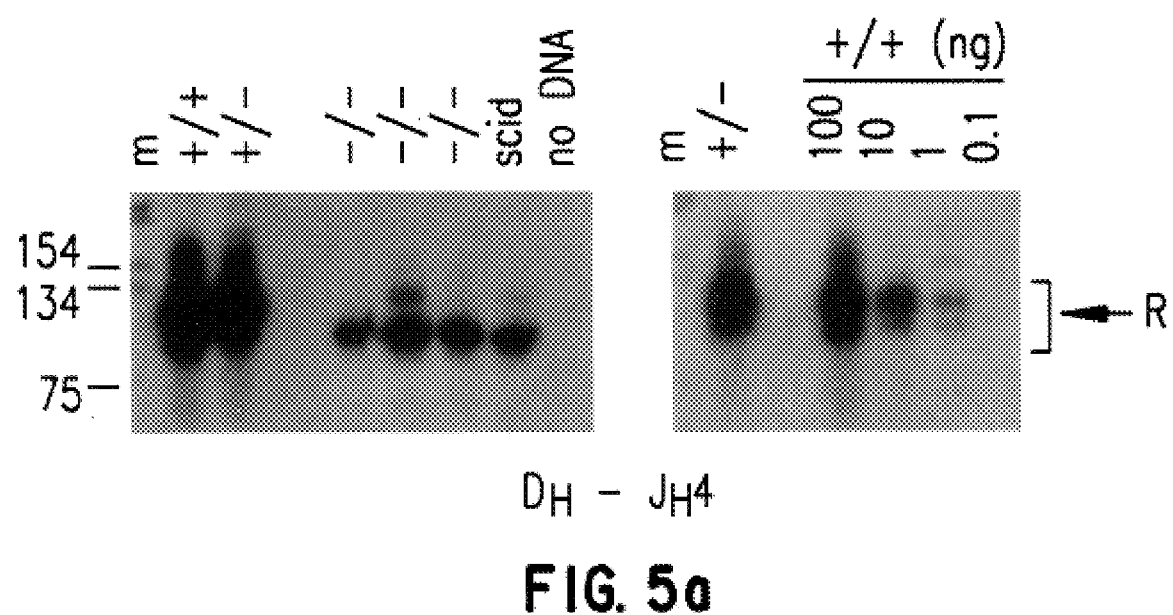
Figure 5B:
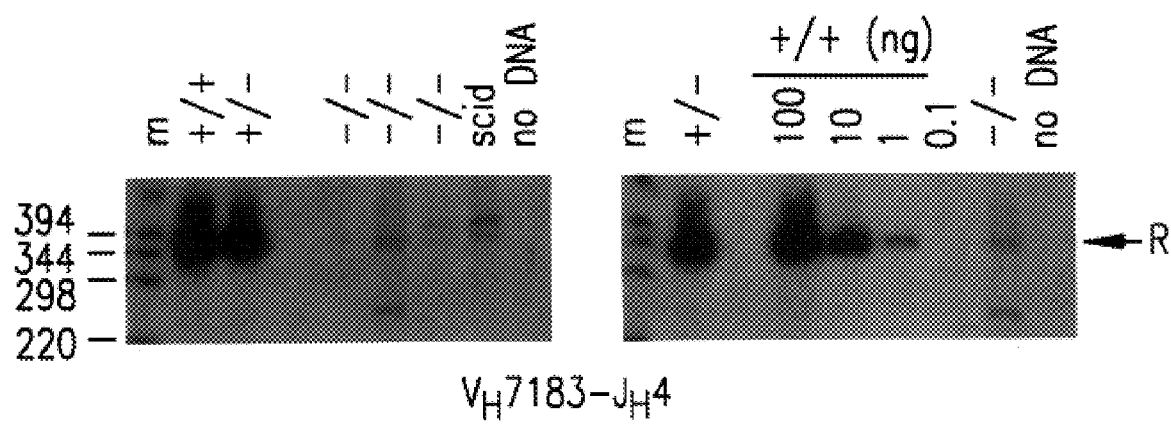

To detect coding joints in the B cell lineage, DNA preparations from bone marrow of individual mice were amplified for Ig heavy chain rearrangements using a semi-quantitative PCR assay. Amplification for D$_H$-J$_H$4 coding joints revealed abundant rearrangements in wild-type or xrcc5$^{M1+/-}$ littermates (FIG. 5a). Rare D-J rearrangements were also detected in xrcc5$^{M1-/-}$ or age matched scid mice. By comparison with products derived from serial dilutions of wild-type DNA, we estimate that the abundance of these rearrangements was decreased approximately 10-fold in scid and xrcc5$^{M1-/-}$ bone marrow (FIG. 5a). Similar levels of D$_H$-J$_H$ coding joints have been detected previously in scid bone marrow (Pennycook et al., 1993, J. Exp. Med. 178:1007–1016). Amplification for V$_H$-J$_H$4 rearrangements detected very low levels of coding joints in both scid and xrcc5$^{M1-/-}$ bone marrow (FIG. 5b), which are at least 100-fold less abundant than in wild-type mice. These data indicate that, as in scid mice, coding joint formation at the Ig heavy chain locus is severely impaired in xrcc5$^{M1-/-}$ mice.

Figure 5C:
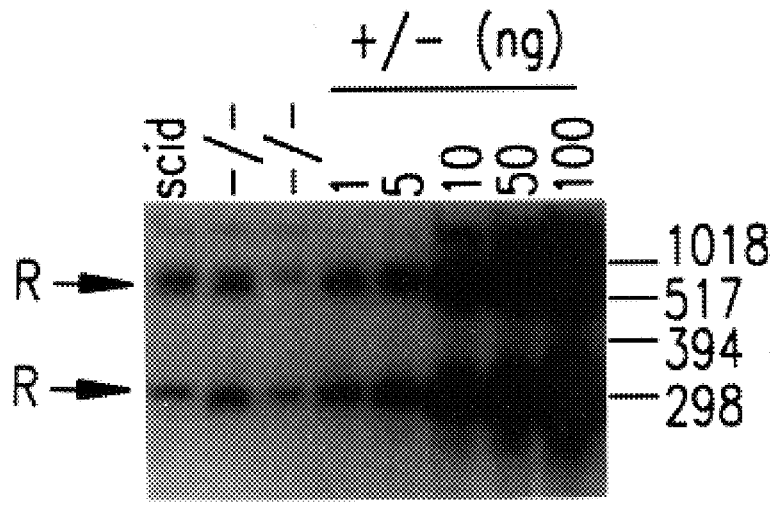
Figure 5D:
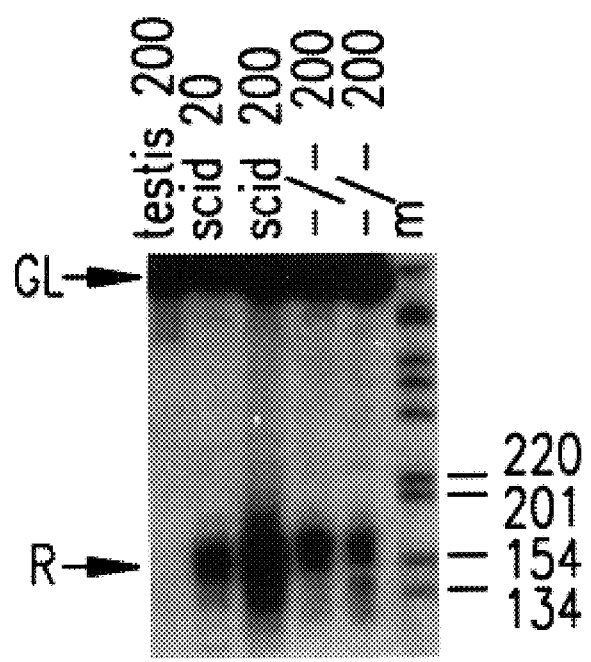

To detect coding joints formed by TCR rearrangement, semiquantitative PCR analysis of thymocyte DNA preparations was performed. We have previously shown that rare coding joints derived from Vβ8-Jβ2.6 joining can be detected by PCR amplification of thymocyte DNA preparations from scid mice (Bogue et al., 1996, Genes Dev. 10:553–565). The same primers were used to amplify thymocyte DNA preparations from newborn scid mice and from two different preparations from 16 day old xrcc5$^{M1-/-}$ mice. Similar amounts of PCR products of the appropriate sizes were detected in all three samples (FIG. 5c). By comparison with a dilution series of DNA from xrcc5$^{M1+/-}$ thymocytes, the abundance of Vβ8-Jβ2.6 coding joints is decreased at least about 100-fold in scid and xrcc5$^{M1-/-}$ thymocytes (FIG. 4c). Thymocyte DNA was also amplified using primers capable of detecting Dδ2-Jδ1 coding joints, which are readily detected in scid thymocytes (Carroll and Bosma, 1991, Genes Dev. 5:1357–1366; Roth et al., 1992). As observed for TCRβ rearrangements, PCR products derived from Dδ2-Jδ1 coding joints were detected in both scid and xrcc5$^{M1-/-}$ thymocytes, although their abundance appears to be somewhat lower in the latter (FIG. 4d). Together with the Ig rearrangement data, these results demonstrate that Ku-deficient mice exhibit a severe defect in coding joint formation, comparable to that observed in scid mice. However, as shown previously in scid mice, a small population of coding ends can apparently bypass the block to coding joint formation in Ku-deficient mice.

Large deletions, which are often observed at endogenous TCR and Ig loci in scid lymphocytes, were also present in Ku-deficient mice, as detected using PCR-based assays (data not shown). These results suggest that Ku function is essential for DNA-PK$_{cs}$ function since xrcc5$^{M1-/-}$ mice are defective in T and B cell development and are defective in coding joint formation as are scid mice.

6.9. impaired formation of signal joints

Figure 5E:
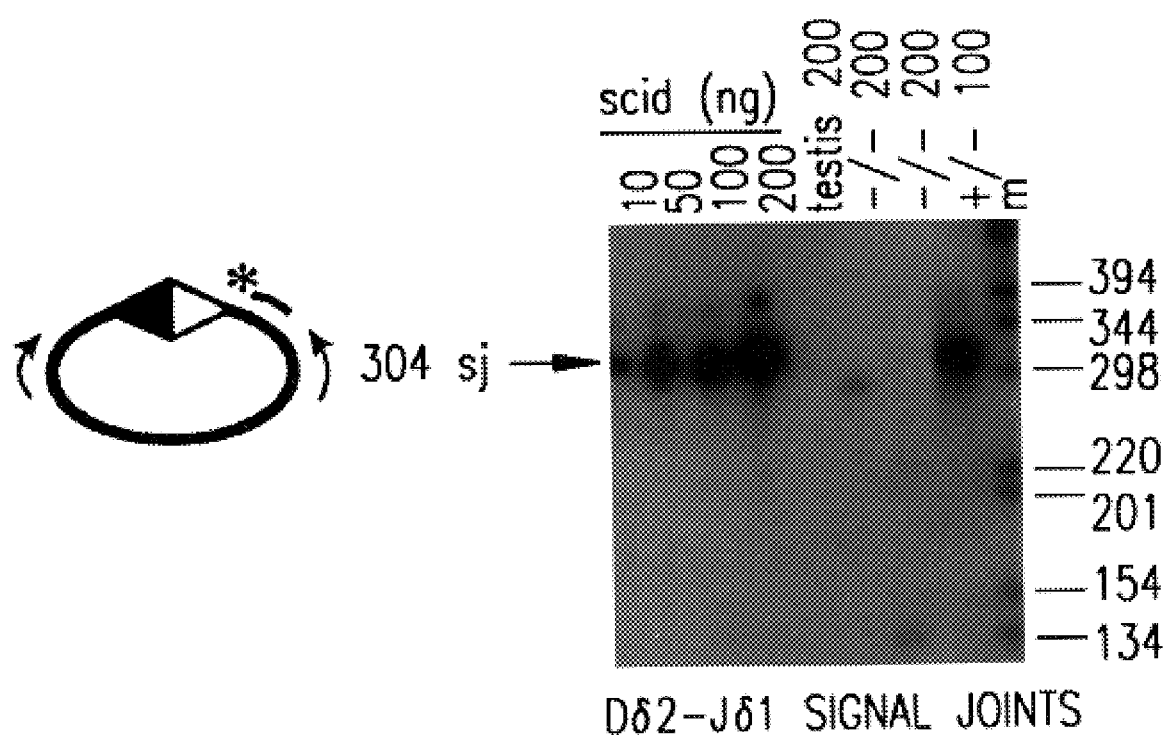

Since Dδ2-Jδ1 coding joints were detected in Ku-deficient mice, a sensitive PCR assay was used to search for the reciprocal products, Dδ2-Jδ1 signal joints. PCR products derived from signal joints were detected in as little as 10 ng of thymocyte DNA from scid mice (FIG. 5e). The identity of these products was further verified by digestion with the restriction enzyme ApaL1 whose recognition site is formed by a perfect signal joint (Roth et al., 1992). Although no PCR products of the appropriate size were apparent after amplification of 200 ng of DNA from two different xrcc5$^{M1-/-}$ thymocyte preparations, rare, smaller products could be detected (FIG. 4e). These PCR products may be derived from signal joints containing deletions as seen previously in xrcc5 mutant cell lines (Taccioli et al., 1993). These data indicate that unlike scid mice, Ku-deficient mice have a severe defect in formation of signal joints, in agreement with previous results from xrcc5 mutant cell lines. These results suggest that Ku may function independent of DNA-PK$_{cs}$ since scid mice do not have a defect in signal joint formation.

6.10. Presence of Hairpin Coding Ends and Full Length Signal Ends

Figure 6A:
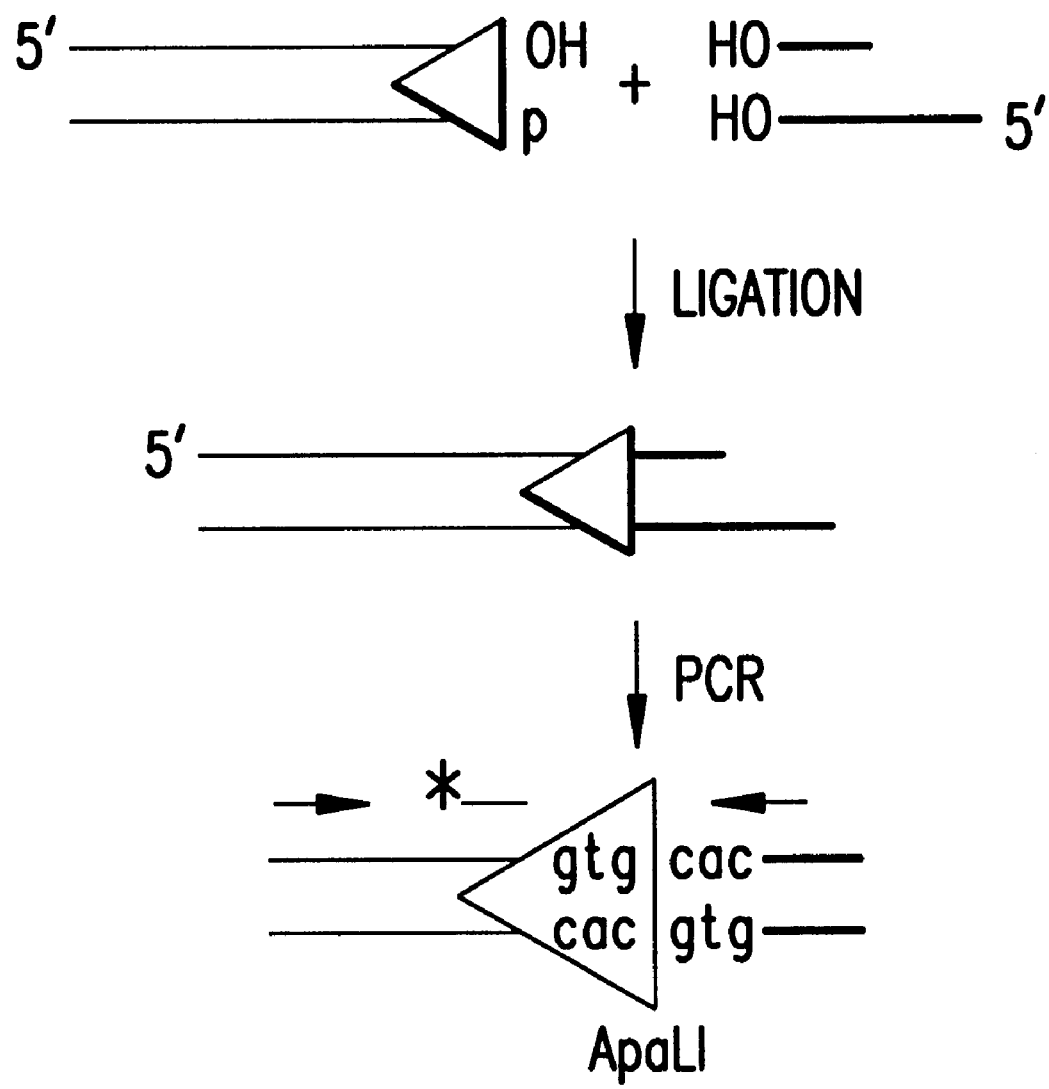

As noted above, Ku has been hypothesized to play a role in stabilizing or protecting the coding and signal ends from degradation. This model predicts that signal ends might be rare in xrcc5$^{M1-/-}$ cells, and, if present, these ends should exhibit loss of nucleotides. To test these predictions, we examined signal ends using a sensitive, semiquantitative ligation-mediated PCR (LMPCR) assay (Roth et al., 1993; Zhu and Roth, 1995, Immunity 2:101–112). This method, schematically illustrated in FIG. 6a, detects broken molecules by ligating a double-stranded oligonucleotide to the broken end, followed by PCR amplification using a primer that hybridizes to the oligonucleotide and a primer specific for the region of interest. Since the short PCR products are displayed on polyacrylamide gels, even the loss of a few nucleotides from the ends would be readily detected. Furthermore, the integrity of the signal ends can be assessed simply by digestion with ApaL1, as only those ends that retain all nucleotides of the RSS will generate an ApaL1 site upon ligation to the oligonucleotide (FIG. 6a).

Figure 6B:
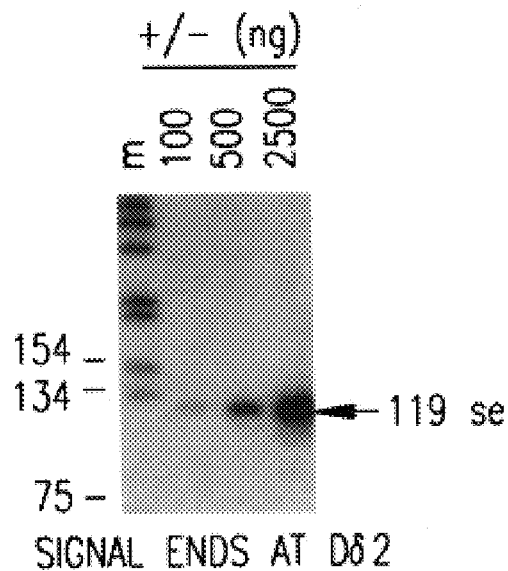
Figure 6C:
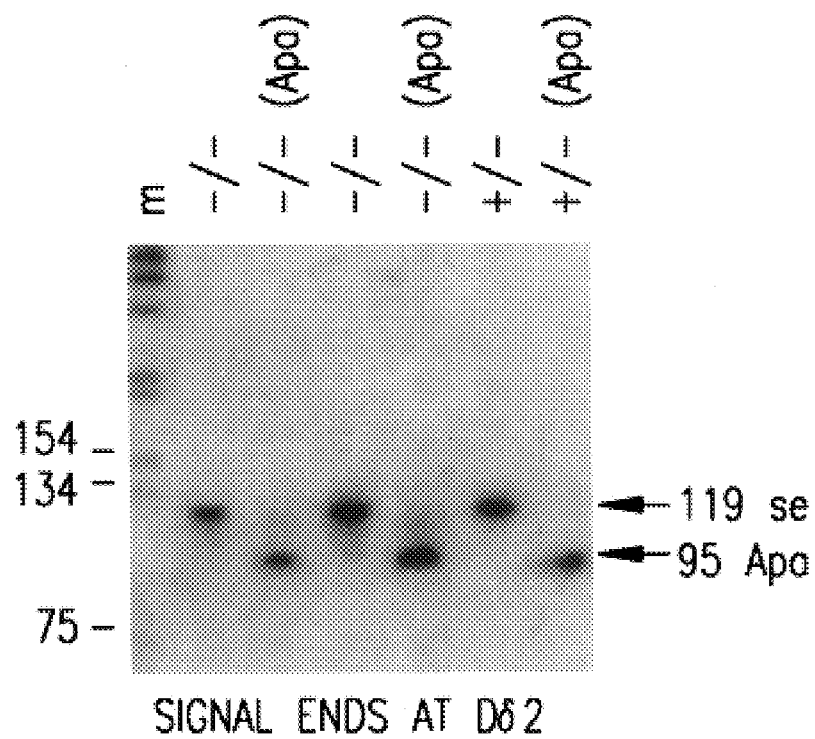

Analysis of signal ends resulting from cleavage at the RSS 5' to Dδ2 is shown in FIG. 6b, demonstrating that the abundance of PCR products obtained from xrcc5$^{M1+/-}$ thymocytes is roughly proportional to the amount of DNA added to the LMPCR assay. PCR products derived from 5' Dδ2 signal ends were observed in two different preparations of thymocyte DNA from xrcc5$^{M1-/-}$ mice (FIG. 6c). The products migrate as single bands, and their abundance is comparable to that of PCR products derived from xrcc5$^{M1+/-}$ or wild-type thymocytes. More than 95% of the products from xrcc5$^{M1-/-}$ thymocytes were cleaved with ApaL1, indicating that the Dδ2 signal ends are preserved, as previously observed in wild-type and scid thymocytes (Roth et al., 1993; Zhu and Roth, 1995). Similar results were obtained by analysis of signal ends derived from cleavage at the RSS on the 3' side of Dδ2.

Figure 6D:
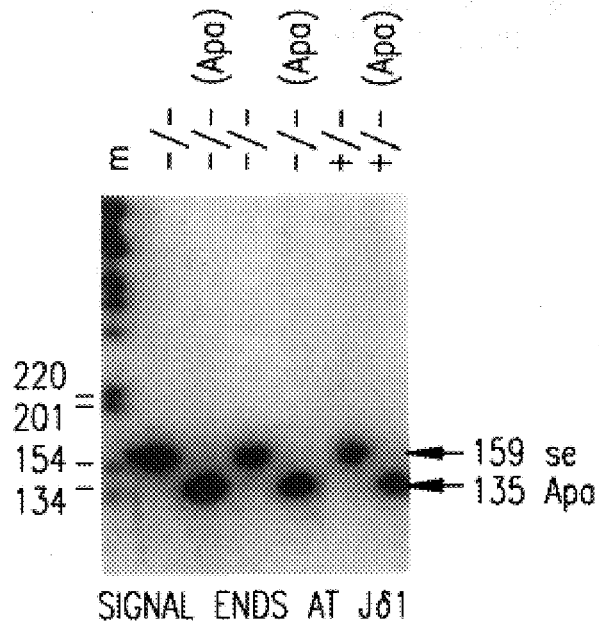
Figure 6E:
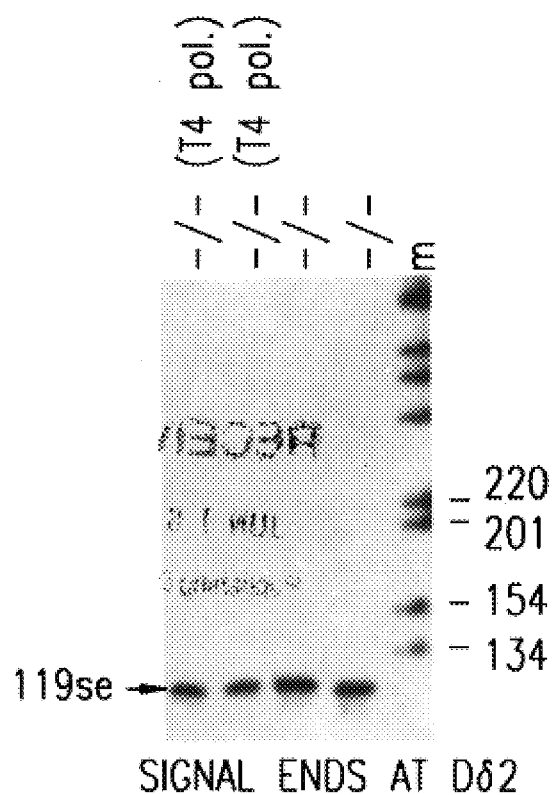

To confirm and extend the above results, Jδ1 signal ends were also analyzed. As observed at Dδ2, LMPCR products derived from signal ends were readily detected in two different thymocyte DNA preparations from xrcc5$^{M1-/-}$ mice (FIG. 6d). Virtually all Jδ1 signal ends were cleaved with ApaL1, indicating that these ends are preserved in Ku-deficient mice. To search for signal ends with non-blunt termini, thymocyte DNA preparations were treated with T4 DNA polymerase prior to ligation to convert any non-flush ends to blunt form. However, non-blunt signal ends were not detected at any of the three loci examined (FIG. 6e). Although these data do not rule out the possibility that low levels of non-blunt signal ends might be present in Ku-deficient mice, the majority of signal ends are flush and full-length, consistent with previous studies of signal ends in wild-type and scid thymocytes (Zhu and Roth, 1995).

Figure 7A:
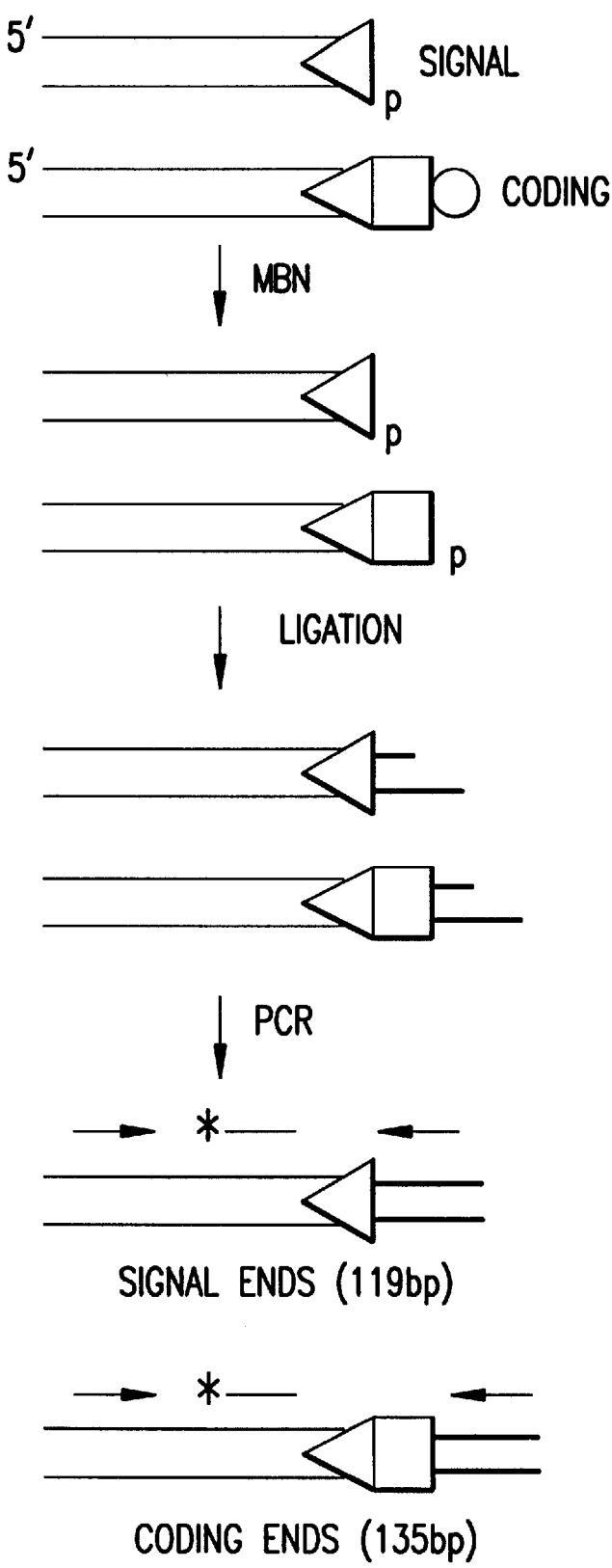

To assess the status of coding ends in thymocytes, the TCR Dδ2 element was studied, which allows detection of both coding ends and signal ends using the same PCR primers, providing a convenient internal control (FIG. 7a). Previous LMPCR and Southern blotting studies of the TCRδ locus have shown that while hairpin coding ends are roughly as abundant as signal ends in scid thymocytes, coding ends cannot be detected in wild-type thymocytes (Roth et al., 1992; Zhu and Roth, 1995). These data suggest that coding ends are joined more rapidly than signal ends and do not accumulate to detectable levels, in agreement with a kinetic analysis performed in a pre-B cell line (Ramsden and Gellert, 1995, Genes Dev. 9:2409–2420).

Blunt coding ends, if present, would be directly ligatable and should generate a PCR product of 135 nt which could be detected in the assay for signal ends (FIG. 6a). However, no such products were detected upon amplification of DNA from xrcc5$^{M1+/-}$ or wild-type thymocytes (FIG. 6b), as shown previously for wild-type and scid thymocytes (Zhu and Roth, 1995). To detect potential coding ends with non-flush termini, DNA samples were pretreated with T4 DNA polymerase to convert single-stranded extensions to blunt form. Again, no coding ends were detected (FIG. 6e). These data indicate that neither flush nor non-flush coding ends accumulate to detectable levels in xrcc5-/- thymocytes, as shown previously in wild-type and scid mice (Zhu and Roth, 1995).

Figure 7B:
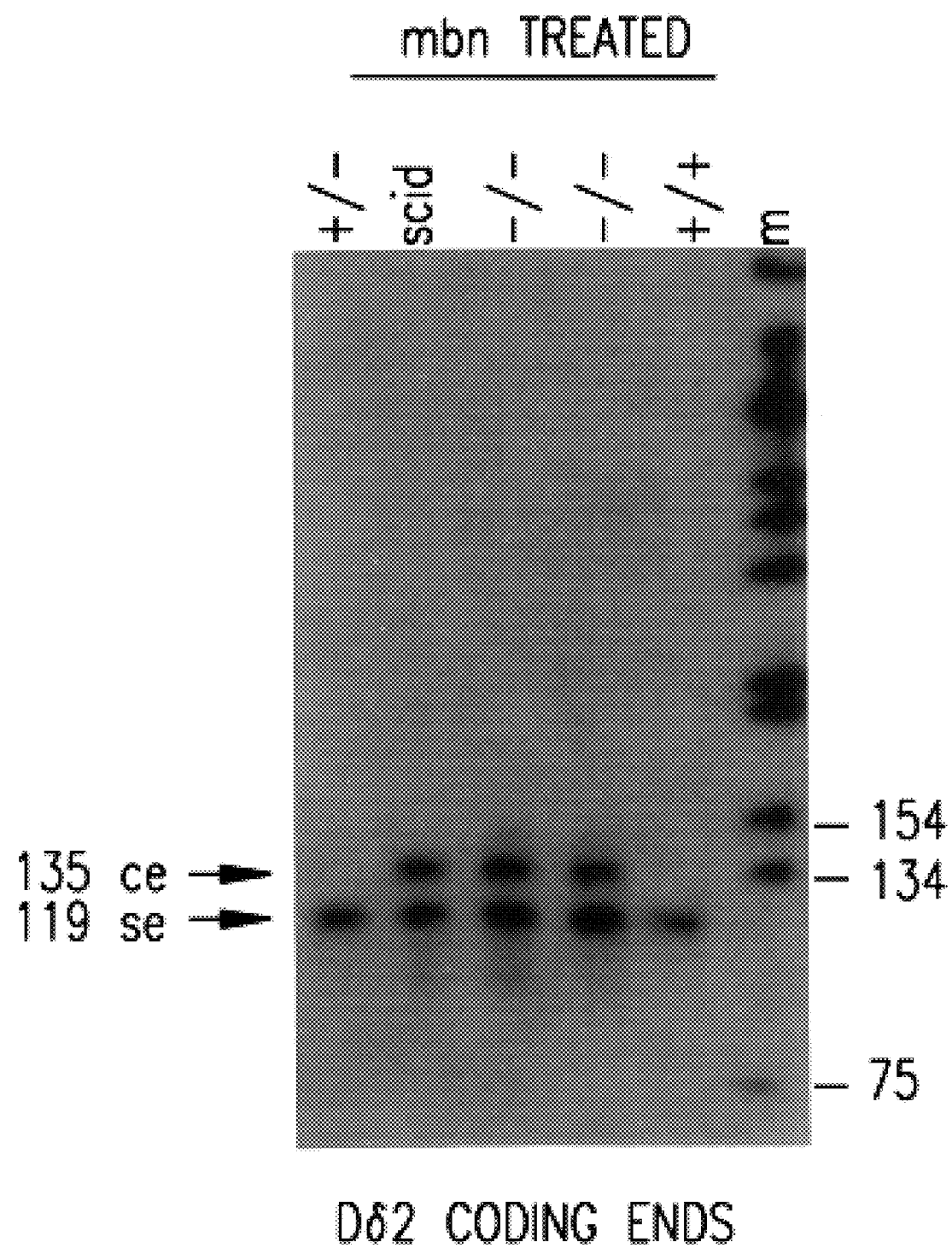

To detect covalently sealed coding ends, DNA preparations were treated with mung bean nuclease (mbn), which opens the hairpins to give ligatable, blunt ends (FIG. 7a). Hairpin coding ends were detected in scid thymocyte DNA (FIG. 7b), as shown previously (Zhu and Roth, 1995). Roughly equivalent levels of coding and signal ends were observed, in agreement with previous Southern blotting studies (Roth et al., 1992). LMPCR of two different thymocyte DNA preparations from xrcc5$^{M1-/-}$ mice generated roughly equal amounts of PCR products derived from both signal and coding ends. As expected, only signal ends were detected in xrcc5$^{M1+/-}$ or wild-type thymocytes. Additional experiments using PCR primers specific for the TCR Dβ1 element also detected hairpin coding ends in samples from scid and Ku-deficient thymocytes, whereas only signal ends were detected in wild-type thymocyte DNA (data not shown). These data indicate that Ku-deficient mice, like scid mice, are defective for processing of hairpin coding ends.

6.11. xrcc5$^{M1}$ Mutant Cells are Hypersensitive to γ-Radiation

Figure 8:
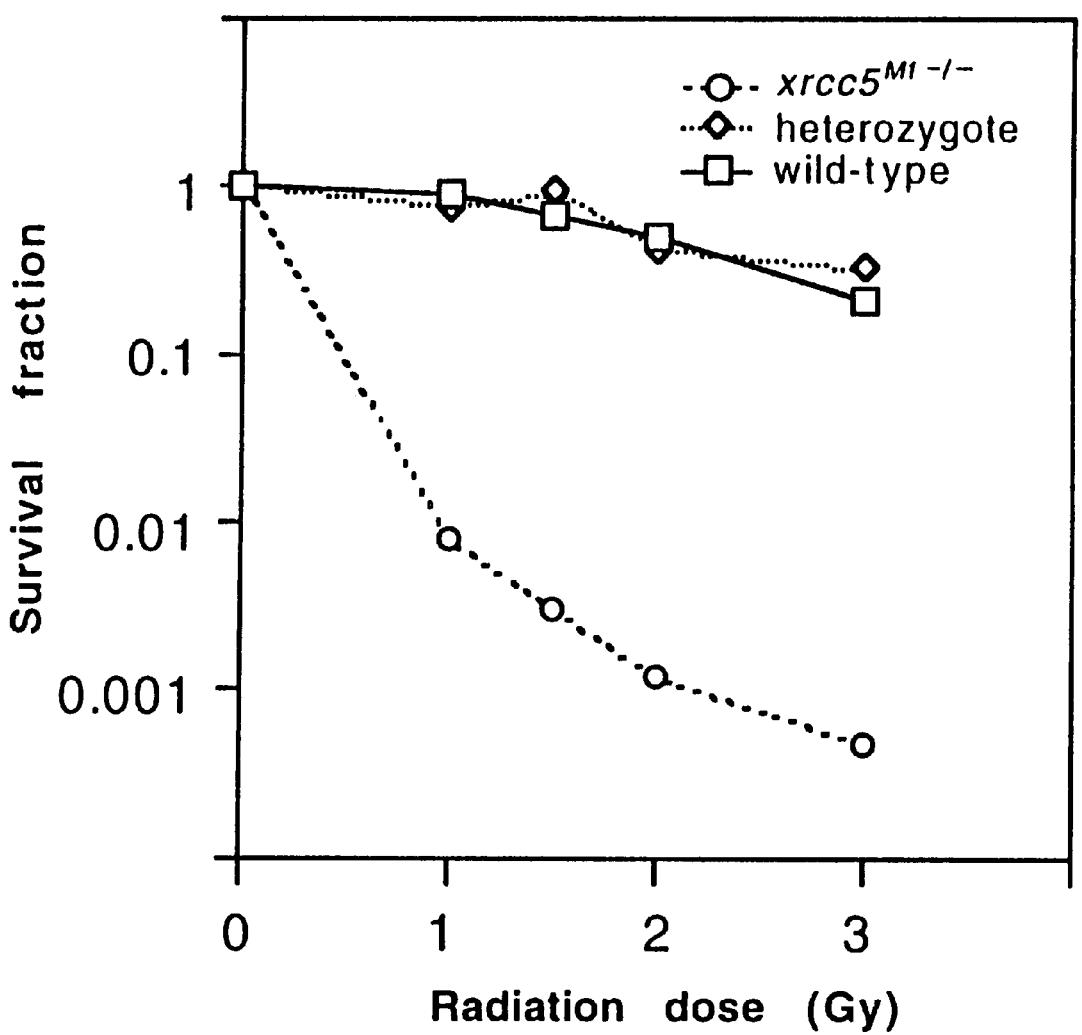

Fibroblasts were derived from xrcc5$^{M1-/-}$ embryos, since Ku has only been analyzed in immortalized cell lines. We predicted that xrcc5$^{M1-/-}$ cells would be hypersensitive to ionizing radiation based on data generated from Ku deficient cell lines (Jeggo, 1990; Weaver, 1995). A dose response curve to γ-radiation was established for xrcc5$^{M1-/-}$ and control (wild-type and xrcc5$^{M1+/-}$) murine embryonic fibroblasts (MEF) and xrcc5$^{M1-/-}$ MEF were hypersensitive to γ-radiation, as predicted (FIG. 8). Ku, in association with DNA-PK$_{cs}$, may directly repair damaged DNA by binding to the genetic lesion and possibly recruiting other proteins to this location. In addition, DNA-PK may influence repair by inhibiting transcription and stimulating a cell cycle response to DNA damage.

6.12. xrcc5$^{M1-/-}$ Mutant Cells Grow Slowly

Figure 9A:
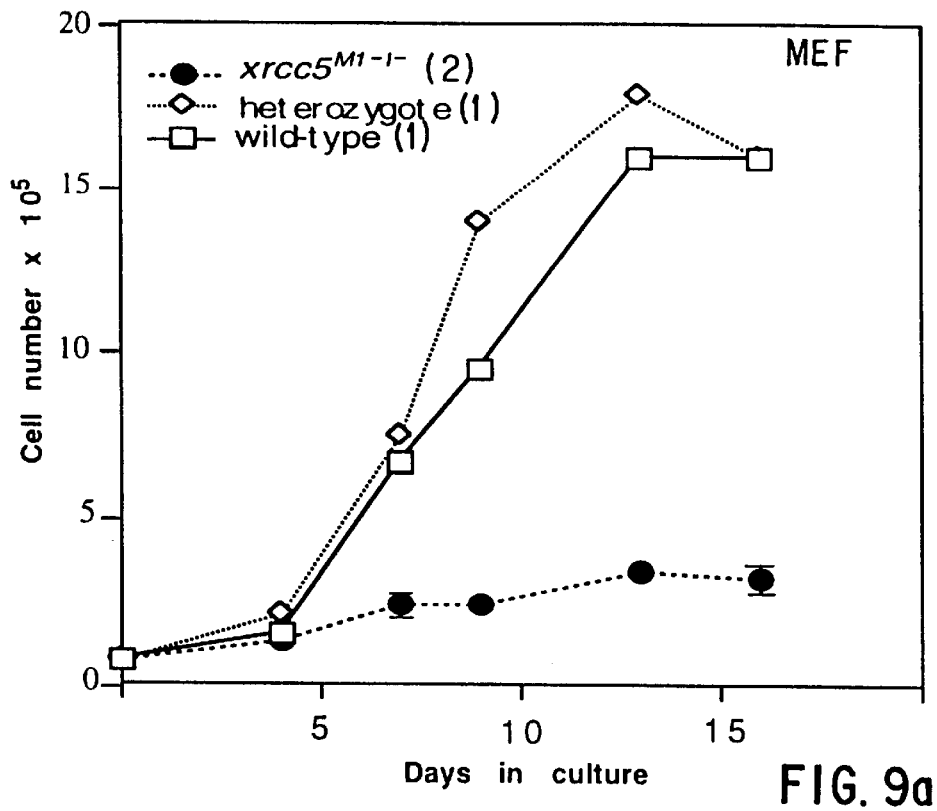
Figure 9B:
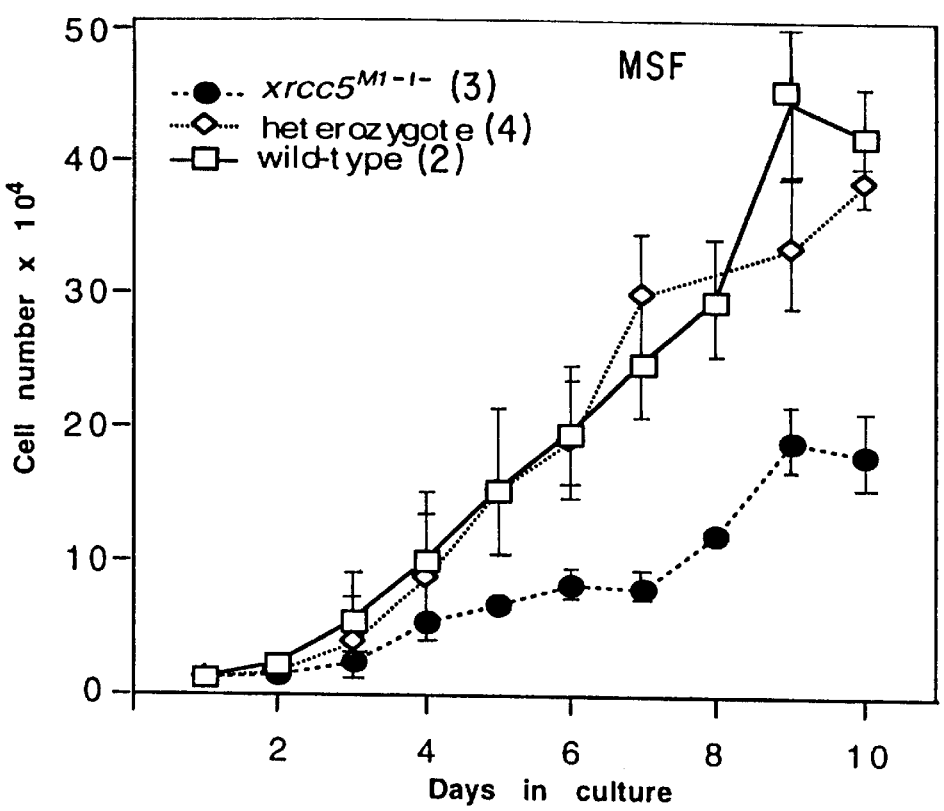
Figure 9C:
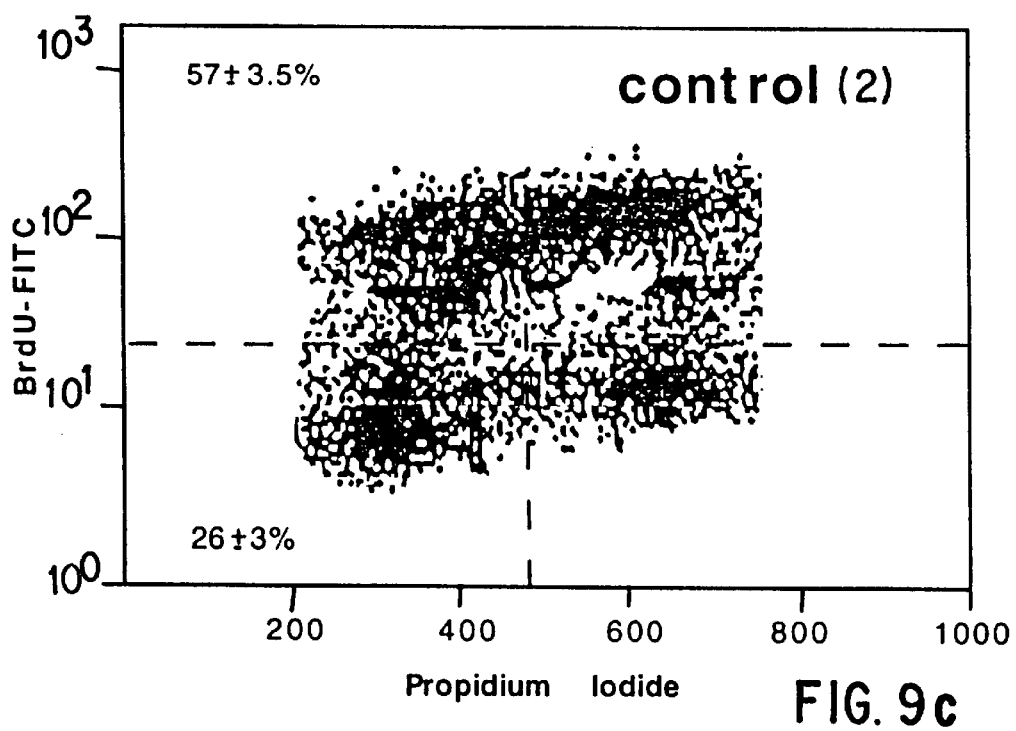
Figure 9D:
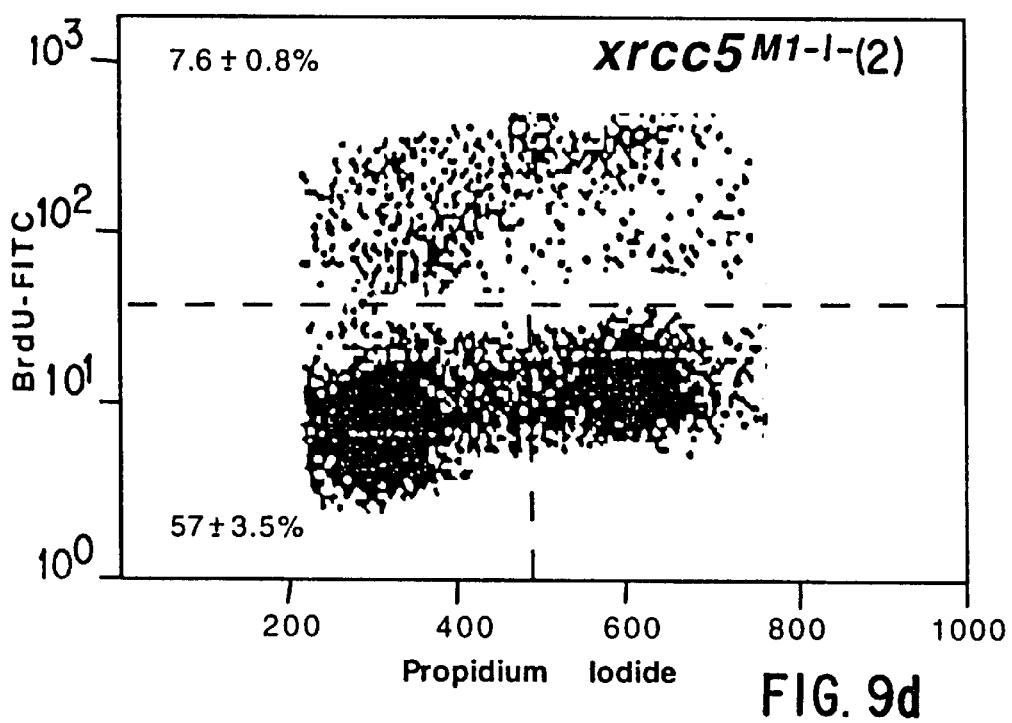

The radiation experiment revealed an unexpected phenotype in xrcc5$^{M1-/-}$ MEF; they appeared to grow slower than control MEF and this defect became more pronounced with increased passage. Growth rates for xrcc5$^{M1-/-}$ and control MEF and mouse skin fibroblast (MSF) were measured after cells were plated at high density. Growth was reduced for both xrcc5$^{M1-/-}$ MEF (FIG. 9a) and xrcc5$^{M1-/-}$ MSF (FIG. 9b). The cell cycle was observed in synchronized MEF by labeling with 5-bromo-2' deoxyuridine (BrdU). Eight-fold fewer xrcc5$^{M1-/-}$ than control MEF entered S phase, possibly due to inefficient progression through the cell cycle which would predict extended cell division time and explain slow growth in tissue culture and in mice (FIG. 9c).

6.13. xrcc5$^{M1-/-}$ Mutant Cells Prematurely Senescence

Figure 10A:
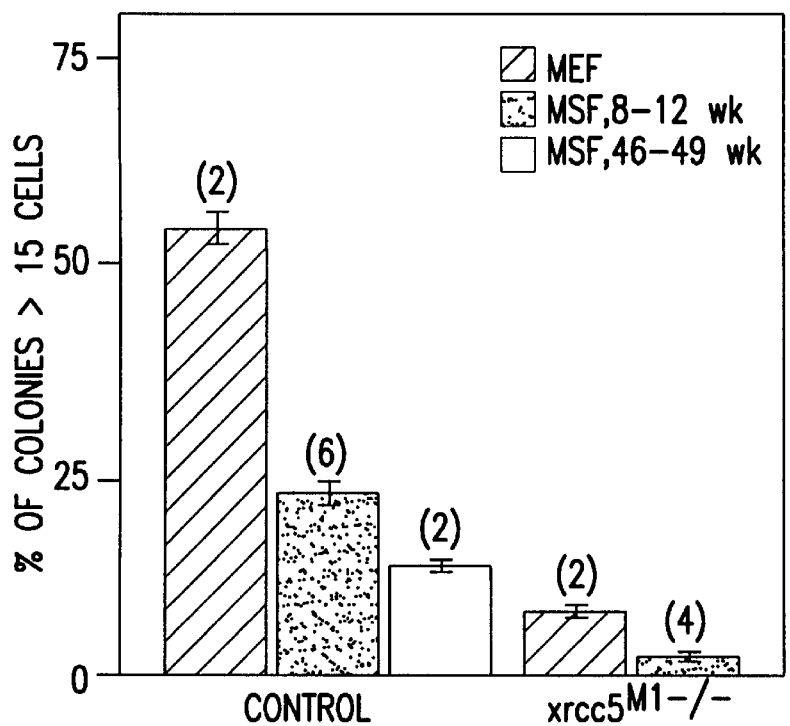

The colony size distributions (CSD) were determined for xrcc5$^{M1-/-}$ and control MEF and MSF to establish their proliferation potentials at low density (FIG. 10a). MEF were generated form 14.5 day embryos and MSF from 8–12 and 46–48 week old mice. The percentage of colonies composed of 4–15 cells (small colonies) and >15 cells (large colonies) was determined. Interestingly, there was an 8 and 11-fold decrease in the percentage of large colonies for xrcc5$^{M1-/-}$ MEF and xrcc5$^{M1-/-}$ MSF, as compared to controls, respectively.

Figure 10B:
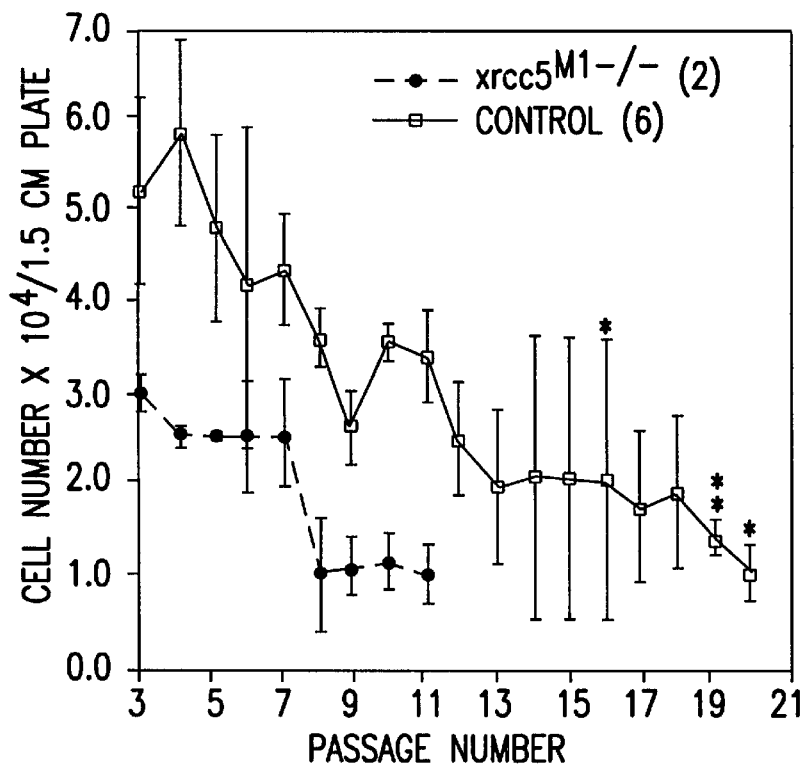
Figure 10C:
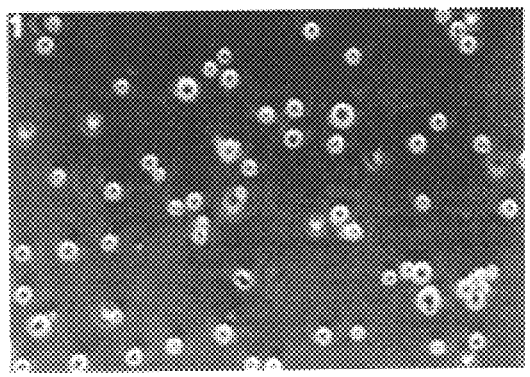
Figure 10D:
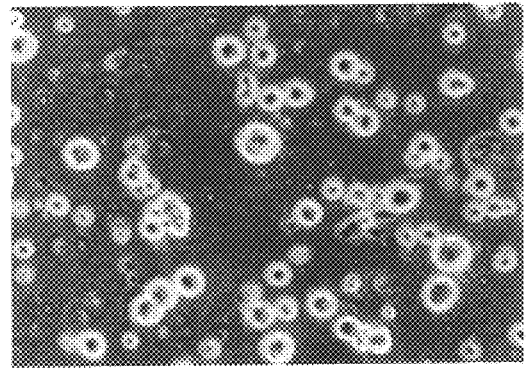
Figure 10E:
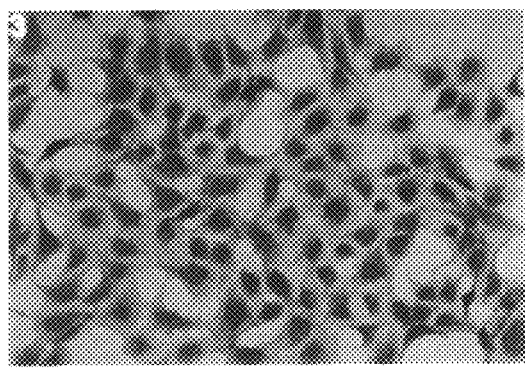
Figure 10F:
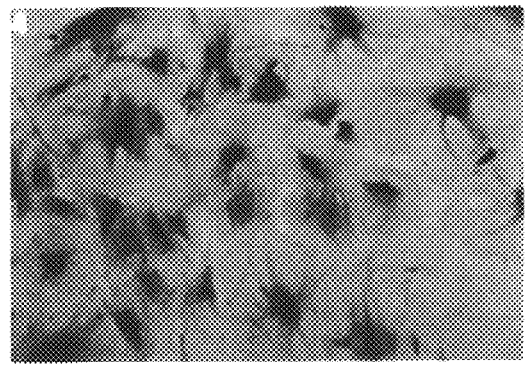

Based on CSD observations, it was predicted that xrcc5$^{M1-/-}$ cells would exhibit premature senescence. CSD accurately predicted age and life span of human embryonic lung and skin fibroblasts and their donors (Smith et al., 1978, Proc. Natl. Acad. Sci., U.S.A. 75:1353–1356; Smith et al., 1980, Mech. Age Dev. 6:283–286). Cells that have undergone numerous passages, either in tissue culture or in vivo, will progressively form a lesser percentage of large colonies. The same observation held true for MEF and MSF because the percentage of large colonies progressively declined with increased donor age for both control and xrcc5$^{M1-/-}$ mice. The life span of xrcc5$^{M1-/-}$ and control MSF was measured by a 3T3 analysis (FIG. 10b). As predicted, xrcc5$^{M1-/-}$ MSF was senescent at an earlier passage than control MSF. In addition, xrcc5$^{M1-/-}$ MEF and xrcc5$^{M1-/-}$ MSF morphology was characteristic of advanced differentiation at a much earlier passage than controls (FIG. 10c), indicating premature senescence (Bayreuther et al., 1988, Proc. Natl. Acad. Sci. U.S.A. 85:5112–5116). These results suggest that Ku may have functions independent from DNA-PK$_{cs}$ since xrcc5$^{M1-/-}$ cells, but not scid cells, rapidly aged in tissue culture.

6.14. screen for rescue of proliferation/aging Defect in xrcc5$^{M1-/-}$ MEF Cells mutant for XRCC5 will be used to screen for genetic mutations that rescue the proliferation/aging defect. The particular type of cell used is unimportant as long as it remains defective for Ku activity. This would include but is not limited to a mutation in XRCC5 or the gene that codes for Ku70.

The mutations to rescue the growth-aging defect in Ku-deficient cells may be made by a variety of techniques and the particular technique employed to make the mutations is not important. Examples of methods of making mutations generally expose cells to DNA damaging agents, preferably agents that do not generated double-strand breaks because it is likely that double-strand breaks will be lethal to these cells. Another method is to infect cells with retrovirus. The integration of the retrovirus will introduce mutations and also serve as a tag. Another method of generating mutations is to generate antisense mRNA by randomly introduced transactivating promoters.

Another approach to rescue proliferation is to ectopically express transgenes in cells deficient for Ku-activity. A variety of expression libraries may be used and the particular kind of library is unimportant. The particular type of cell used is unimportant as long as it is defective in Ku activity. This would include but is not limited to a mutation in XRCC5 or the gene that codes for Ku70.

Another approach to rescue proliferation is to induce over expression of endogenous genes in cells deficient for Ku-activity. A variety of techniques may be used and the particular kind of technique is unimportant. The particular type of cell used is unimportant other than it is defective in Ku activity. This would include but is not limited to a mutation in XRCC5 or the gene that code for Ku70.

Another approach to rescue the proliferation/aging phenotype is to breed Ku-deficient mice with mice deficient for tumor suppresser genes or any gene that negatively regulates the cell cycle which would include but is not limited to p53 mutant mice and p21 mutant mice. Rescue of the proliferation/aging defect may be analyzed in cells derived from these mice and/or in the mice.

Another approach to rescue the proliferation/aging phenotype is to breed Ku-deficient mice with genetically altered mice that promote progression through the cell cycle which would include, but is not limited to, mice that overexpress oncogenes. Rescue of the proliferation/aging defect may be analyzed in cells derived from these mice and/or in the mice.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. A knockout mouse comprising a disruption in at least one allele of its endogenous XRCC5 gene, wherein said disruption prevents transcription of messenger RNA from said allele of the XRCC5 gene and results in a reduced level of KU autoantigen in said knockout mouse compared to a mouse without said disruption.

2. A mouse of claim 1, wherein said disruption is a deletion.

3. A mouse according to claim 1, said mouse being characterized by abnormal immune cell development.

4. A mouse according to claim 1, said mouse being characterized by hypersensitivity to gamma-radiation.

5. A mouse according to claim 1, said mouse being characterized by an abnormally small body size.

6. A mouse according to claim 1 wherein said mouse is homozygous for said mutation in the XRCC5 gene.

7. A mouse according to claim 1 wherein said disruption deletes nucleotides 701–964 of the XRCC5 coding sequence as set forth in SEQ ID NO:1.

8. An isolated mouse cell comprising a deletion mutation in at least one allele of the XRCC5 gene, wherein the level of KU autoantigen is reduced compared to mouse cells without said deletion mutation.

9. A cell according to claim 8 wherein said mutation deletes nucleotides 701–964 of the XRCC5 coding sequence as set forth in SEQ ID NO:1.

10. An isolated mouse cell comprising a mutation in at least one allele of the XRCC5 gene, wherein the level of KU autoantigen is reduced compared to mouse cells without said mutation.

11. A cultured mammalian cell comprising a deletion mutation in at least one allele of the XRCC5 gene, wherein the level of KU autoantigen is reduced compared to mammalian cells without said deletion mutation.

12. A cultured mammalian cell comprising a mutation in at least one allele of the XRCC5 gene, wherein the level of KU autoantigen is reduced compared to mammalian cells without said mutation.

13. A method for identifying a mutation that rescues the phenotype of $xrcc5^{M1-/-}$ cells, comprising the steps of:

(A) providing cells which have a homozygous disruption in its $xrcc5^{M1}$ gene, (B) introducing a mutation into said cells, wherein said mutation is a defined mutation in an endogenous nucleic acid of said cells or is comprised in an exogenous nucleic acid, (C) growing said cells, (D) performing a 3T3 or 3T9 or population doubling analysis to select cells that do not become senescent after passage 8;

wherein a mutation that rescues the phenotype of said $xrcc5^{M1-/-}$ cells is identified.

14. A method according to claim 13 wherein said mutation is introduced into said cells by transfecting a nucleic acid comprising said mutation into said cells.

15. A method according to claim 13 wherein said introduction of a mutation results in overexpression of an endogenous gene in said mouse cells.

* * * * *